(12) United States Patent
Bauer et al.

(10) Patent No.: US 7,446,086 B2
(45) Date of Patent: Nov. 4, 2008

(54) AGENTS THAT ARE ABSORBED ON THE SURFACES OF SUBSTRATES

(75) Inventors: Andreas Bauer, Kaarst (DE); Wolfgang Lahn, Willich (DE); Werner Faber, Willich (DE); Georg Meine, Mettmann (DE)

(73) Assignee: Henkel Kommanditgesellschaft auf Aktien, Dusseldorf (DE)

( * ) Notice: Subject to any disclaimer, the term of this patent is extended or adjusted under 35 U.S.C. 154(b) by 18 days.

(21) Appl. No.: 11/354,645

(22) Filed: Feb. 15, 2006

(65) Prior Publication Data

US 2006/0229230 A1 Oct. 12, 2006

Related U.S. Application Data

(63) Continuation of application No. PCT/EP2004/008938, filed on Aug. 10, 2004.

(30) Foreign Application Priority Data

Aug. 19, 2003 (DE) ................. 103 38 070

(51) Int. Cl.
*C11D 1/38* (2006.01)
*C11D 3/37* (2006.01)
*C11D 3/50* (2006.01)
*D06L 1/00* (2006.01)
*B08B 3/04* (2006.01)

(52) U.S. Cl. .............. 510/466; 510/122; 510/123; 510/330; 510/475; 510/504; 424/70.12; 8/137; 134/25.2; 134/42

(58) Field of Classification Search ........... 510/122, 510/123, 330, 466, 475, 504; 424/70.12; 8/137; 134/25.2, 42
See application file for complete search history.

(56) References Cited

U.S. PATENT DOCUMENTS

| | | | |
|---|---|---|---|
| 3,158,615 A | 11/1964 | Dunn | |
| 3,234,258 A | 2/1966 | Morris | |
| 4,524,009 A | 6/1985 | Valenty | |
| 4,639,325 A | 1/1987 | Valenty | |
| 4,664,839 A | 5/1987 | Rieck | |
| 4,816,553 A | 3/1989 | Baur | |
| 4,820,439 A | 4/1989 | Rieck | |
| 4,985,553 A | 1/1991 | Fuertes | |
| 5,075,041 A | 12/1991 | Lutz | |
| 5,107,180 A | 4/1992 | Ormanns | |
| 5,356,607 A | 10/1994 | Just | |
| 5,422,280 A | 6/1995 | Helliwell | |
| 5,494,488 A | 2/1996 | Arnoldi | |
| 5,501,814 A | 3/1996 | Engelskirchen | |
| 5,541,316 A | 7/1996 | Engelskirchen | |
| 5,580,941 A | 12/1996 | Krause | |
| 5,705,169 A | 1/1998 | Stein | |
| 5,730,960 A | 3/1998 | Stein | |
| 5,780,420 A | 7/1998 | Breuer | |
| 5,821,360 A | 10/1998 | Engelskirchen | |
| 5,830,956 A | 11/1998 | Stockhausen | |
| 5,858,939 A | 1/1999 | Tsaur | |
| 5,922,670 A | 7/1999 | Knuebel | |
| 5,958,870 A | 9/1999 | Declercq | |
| 5,959,101 A | 9/1999 | Engelskirchen | |
| 6,037,315 A * | 3/2000 | Franklin et al. ............. 510/123 |
| 6,187,055 B1 | 2/2001 | Kottwitz | |
| 2004/0072704 A1 | 4/2004 | Gerke | |

FOREIGN PATENT DOCUMENTS

| | | |
|---|---|---|
| CA | 2 029 542 C | 5/1991 |
| DE | 38 08 114 A1 | 9/1989 |
| DE | 40 14 055 C2 | 11/1991 |
| DE | 42 21 381 C1 | 2/1994 |
| DE | 43 00 772 C2 | 7/1994 |
| DE | 43 03 320 C2 | 8/1994 |
| DE | 43 21 022 A1 | 1/1995 |
| DE | 44 00 024 A1 | 7/1995 |
| DE | 44 17 734 A1 | 11/1995 |
| DE | 195 13 391 A1 | 10/1996 |
| DE | 195 40 086 A1 | 4/1997 |
| DE | 196 00 018 A1 | 7/1997 |
| DE | 197 12 033 A1 | 9/1998 |
| EP | 0 046 070 B1 | 2/1982 |
| EP | 0 150 930 | 8/1984 |
| EP | 0 164 514 B1 | 12/1985 |

(Continued)

OTHER PUBLICATIONS

Schulze, K., et al., "Fettalkoholoxathylatacetate," Seifen-Ole-Fette-Wachse 101:37-41, (1975).

(Continued)

*Primary Examiner*—Brian P Mruk
(74) *Attorney, Agent, or Firm*—John S. Child, Jr.

(57) ABSTRACT

A detergent, cleaning, conditioning or cosmetic agent that is absorbed by the surface of substrates and that contains oligomers, polymers or copolymers comprising a specific structural element. The agent may also form part of a conditioning substrate, wherein the substrate, such as a fleece material, is saturated and/or coated with the agent. The agent may also be used in a process for treating hard and/or soft substrate surfaces comprising the step of applying an effective quantity of the agent to the substrate.

42 Claims, No Drawings

FOREIGN PATENT DOCUMENTS

| | | |
|---|---|---|
| EP | 0 232 202 B1 | 8/1987 |
| EP | 0 280 223 B1 | 8/1988 |
| EP | 0 427 042 B1 | 5/1991 |
| EP | 0 427 349 | 5/1991 |
| EP | 0 542 496 B1 | 5/1993 |
| EP | 0 693 471 B1 | 1/1996 |
| EP | 0 693 741 A2 | 1/1996 |
| EP | 0 694 521 B1 | 1/1996 |
| EP | 0 727 448 B1 | 8/1996 |
| EP | 0 728 749 B1 | 8/1996 |
| EP | 0 771 785 B1 | 5/1997 |
| EP | 0 799 855 B1 | 10/1997 |
| EP | 818 450 B1 | 1/1998 |
| EP | 0 982 022 A2 | 3/2000 |
| EP | 0 982 023 B1 | 3/2000 |
| EP | 0 982 313 | 3/2000 |
| EP | 982022 * | 3/2000 |
| EP | 0 998 911 A2 | 5/2000 |
| JP | 58-217598 | 12/1983 |
| JP | 5-339896 | 12/1993 |
| WO | WO 90/13533 | 11/1990 |
| WO | WO 91/08171 | 6/1991 |
| WO | WO 92/18542 | 10/1992 |
| WO | WO 93/08251 | 4/1993 |
| WO | WO 93/16110 | 8/1993 |
| WO | WO 93/23603 | 11/1993 |
| WO | WO 94/28030 | 12/1994 |
| WO | WO 95/07303 | 3/1995 |
| WO | WO 95/07331 | 3/1995 |
| WO | WO 95/12619 | 5/1995 |
| WO | WO 95/19953 | 7/1995 |
| WO | WO 95/19954 | 7/1995 |
| WO | WO 95/19955 | 7/1995 |
| WO | WO 95/20029 | 7/1995 |
| WO | WO 95/20608 | 8/1995 |
| WO | WO 96/23768 | 8/1996 |
| WO | WO 96/38528 | 12/1996 |
| WO | WO 01/68037 A2 | 9/2001 |

OTHER PUBLICATIONS

Holzbauer, H.R., et al., "n-Octyl-polyoxypropylencarboxymethoylate," Tenside Surfactants Detergents, 25:308-311, (1988).

Domsch, A., and B. Irrgang, "Anionic Surfactants: organic chemistry," Stache, H.W., editor, Surfactant science series, vol. 56:501-549, Marcel Dekker, Inc., New York, (1996).

CTFA Cosmetic Ingredient Dictionary (The Cosmetic, Toiletry and Fragrance, Inc., 1997), vol. 1, 2, and 3, Wenninger, J.A., et al. editors.

International Cosmetic Ingredient Dictionary and Handbook, (The Cosmetic, Toiletry and Fragrance, Inc., 2000), vol. 1, Wenninger, J.A., et al., editors.

Finkel, P., SoFW Journal, vol. 122, p. 543 (1996).

* cited by examiner

AGENTS THAT ARE ABSORBED ON THE SURFACES OF SUBSTRATES

CROSS-REFERENCE TO RELATED APPLICATIONS

This application is a continuation under 35 U.S.C. § 365(c) and 35 U.S.C. § 120 of International Application PCT/EP2004/008938, filed Aug. 10, 2004. This application also claims priority under 35U.S.C. § 119 of DE 103 38 070.1, filed Aug. 19, 2003. Both the International application and the German application are incorporated herein by reference in their entireties.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The present invention relates to agents, comprising oligomers, polymers or copolymers, which comprise a specific structural element and in addition a compound that preferably carries at least one cationic charge and is absorbed on hard and/or soft surfaces of substrates, as well as the use of such agents. The invention further relates to a conditioning substrate and processes for conditioning textiles as well as for treating substrate surfaces.

(2) Description of Related Art, Including Information Disclosed Under 37 C.F.R. §§ 1.97 and 1.98

The European Patent applications EP 0 998 911 A2, EP 0 982 313 A2 and EP 0 982 022 A2 of General Electric describe non-volatile polymers, copolymers or oligomers of siloxanes, in which one or more organic substituents are derived from specific alcohols, aldehydes, ketones or ester groups, which lend specific advantageous properties to the siloxanes themselves and also to compositions into which the respective siloxanes have been incorporated.

However, it is ignored how one can provide agents according to EP 0 998 911 A2, EP 0 982 313 A2 and EP 0 982 022 A2 which are characterized in that the compounds, present in said agents, are better absorbed on the substrates to be treated with the agent.

BRIEF SUMMARY OF THE INVENTION

Accordingly, the object of the present invention is to provide agents that comprise compounds that possess a specific structure, borrowed from one of the publications EP 0 998 911 A2, EP 0 982 313 A2 and EP 0 982 022 A2, which demonstrates specific advantageous properties, wherein the agents ensure that the compounds are better absorbed on the substrates to be treated.

Accordingly, the subject of the invention is an agent, particularly a detergent or cleaning agent or conditioner or cosmetic, including at least one compound that preferably carries at least one cationic charge and which is absorbed on hard and/or soft surfaces of substrates, as well as at least one oligomer, polymer or copolymer that comprises the following structural element shown in Formula (1) at least once,

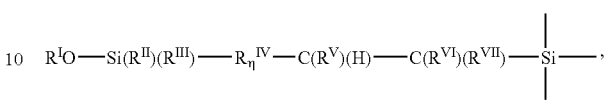

wherein $R^{II}$, $R^{III}$, independently of one another each stand for an aliphatic or aromatic, linear or branched, saturated or unsaturated, substituted or unsubstituted hydrocarbon group that, as appropriate, can comprise heteroatoms such as oxygen, nitrogen, sulfur or halogens or others. Preferred groups $R^{II}$, $R^{III}$ are alkyl and/or alkoxy groups, for example methyl or methoxy groups. $R_\eta^{IV}$ stands for a carbon-bridging moiety. This carbon-bridging moiety is an aliphatic or aromatic, linear or branched, saturated or unsaturated, substituted or unsubstituted hydrocarbon group that, as appropriate, can comprise heteroatoms such as oxygen, nitrogen, sulfur or halogens or others. Preferably however, the carbon-bridging moiety is an aliphatic hydrocarbon group. The variable $\eta$ ranges from 0 to 10. This means that the group $Si(R^{II})(R^{III})$ of Formula (1) can also be directly bonded to the group $C(R^V)(H)$ of Formula (1), such that in a preferred embodiment there is no carbon-bridging moiety. This is the case when $\eta=0$.

$R^V$, $R^{VI}$, $R^{VII}$ independently of each other each stand for hydrogen or an aliphatic or aromatic, linear or branched, saturated or unsaturated, substituted or unsubstituted hydrocarbon group that, as appropriate, can comprise heteroatoms such as oxygen, nitrogen, sulfur or halogens or others. Preferred $R^V$, $R^{VI}$, $R^{VII}$ groups are hydrogen or alkyl groups.

The remaining three valences of the terminal silicon in Formula (1) are satisfied, independently of each other, by any oligomeric, polymeric or copolymeric group. Preferably, up to two of these groups are alkyl groups, particularly methyl groups.

$R^I O$ represents either a group that is a fragrance-alkoxy group and/or a biocide-alkoxy group, derived from the corresponding fragrance and/or biocide alcohol $R^I OH$, or $R^I O$ represents a group, derived from an enolizable fragrance and/or or biocide ester, ketone or aldehyde.

An arbitrary example (a), in which $R^I O$ represents a group, which is derived from an enolizable fragrance aldehyde, would be

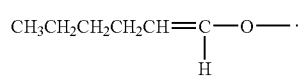

The enolizable aldehyde in this example (a) is hexanal,

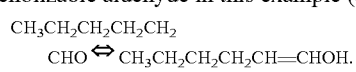

keto form enol form.

An arbitrary example (b) for an inventive compound that comprises the structural element

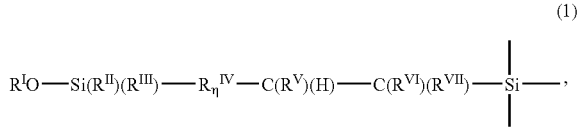

(1)

at least once, is consequently the following compound:

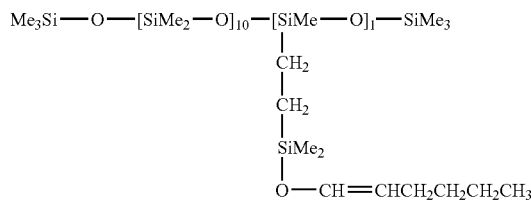

(b)

The assignments are as follows:

| | | |
|---|---|---|
| $R^IO$ | corresponds to | $CH_3CH_2CH_2CH_2CH=CH—O—$ |
| $Si(R^{II})(R^{III})$ | corresponds to | $SiMe_2—$ |
| $R_\eta^{IV}$ | when $\eta$ equals $0 \rightarrow$ | no bridging moiety |
| $C(R^V)(H)$ | corresponds to | $CH_2—$ |
| $C(R^{VI})(R^{VII})$ | corresponds to | $CH_2—$ |

The three remaining valences of the terminal silicon in Formula 1 are satisfied by different oligomeric groups, one being a methyl group.

A further arbitrary example (c) for an inventive compound that comprises the structural element

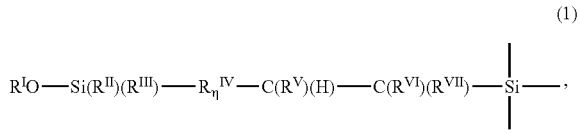

(1)

at least once is also the following compound, which differs from the inventive compound listed in the previous example solely in the group $R^IO—$:

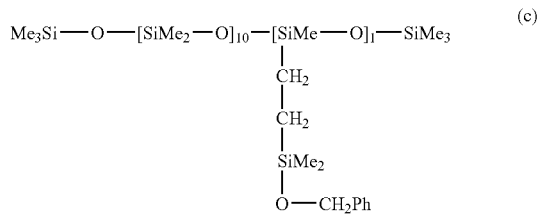

(c)

The assignments are as follows:

| | | |
|---|---|---|
| $R^IO$ | corresponds to | $PhCH_2O$ |
| $Si(R^{II})(R^{III})$ | corresponds to | $SiMe_2$ |
| $R_\eta^{IV}$ | when $\eta$ equals $0 \rightarrow$ | no bridging moiety |
| $C(R^V)(H)$ | corresponds to | $CH_2$ |
| $C(R^{VI})(R^{VII})$ | corresponds to | $CH_2$ |

The three remaining valences of the terminal silicon in Formula 1 are satisfied by different oligomeric groups, one being a methyl group.

In this exemplary compound (c), $R^IO$ represents a group that is derived from a fragrance alcohol, namely $PhCH_2OH$. In the exemplary compound (b), $R^IO$ represents a group that is derived from an enolizable fragrance aldehyde, namely hexanal.

Advantageous embodiments of such an agent are fragrant agents, biocides and/or fragrant biocides. Thus, these agents can release fragrances and/or biocides and/or biocidal fragrances, such that a fragrance is emitted both from the agents and also from substrates treated with the agents and/or that both the agent and also the agent-treated substrate can release biocides and/or that both the agent and also the agent-treated substrate can have both a fragrant effect and also release biocides. Advantageously, the release of the fragrance or the biocide occurs slowly, such that a longer lasting fragrance effect is obtained in comparison with conventional agents.

BRIEF DESCRIPTION OF THE SEVERAL VIEWS OF THE DRAWING(S)

Not Applicable

DETAILED DESCRIPTION OF THE INVENTION

In the context of the present invention, the term "fragrance" is understood to mean all perfumes or materials or their mixtures which people perceive as odors and which trigger a sensation of smell, preferably a pleasant sensation of smell in humans. Accordingly, in the context of the invention, "fragrance alcohols" are fragrances or perfumes, which possess a free hydroxyl group, irrespective of how the molecule is further constructed. Analogously, fragrance-esters, ketones, aldehydes designate those fragrances, which possess free ester, keto or aldehyde functionalities, respectively. This implies that in the context of this invention, certain molecules, such as, for example esters of salicylic acid can act, for example, as both a fragrance alcohol and also a fragrance ester. Preferred representatives can be named from the extensive group of the fragrance alcohols, esters, ketones and aldehydes. These preferred representatives will be named in the course of this patent document.

Analogously, biocide alcohols, aldehydes, esters and ketones are understood to mean all compounds which possess alcohol, aldehyde, ester or keto functionality in the above sense, and which are capable of at least inhibiting germ growth. Preferred representatives will also be named in the course of this patent document.

The terms "fragrance-alkoxy group" and "biocide-alkoxy group" agree with what was previously said in that they are the corresponding anions of the relevant fragrance alcohols or biocide alcohols resulting from the abstraction of a hydrogen atom.

It was determined that the combined addition of the inventive oligomers, polymers or copolymers with at least one compound that preferably carries at least one cationic charge and is absorbed on hard and/or soft surfaces of substrates, in appropriate agents, preferably agents for treating textiles, leads to a particularly long lasting substrate fragrancy in addition to a long lasting product fragrancy, wherein the compound that preferably carries at least one cationic charge and is absorbed on hard and/or soft surfaces of substrates affords a particularly advantageous affinity of the inventive oligomers, polymers or copolymers to the treated substrate, which advantageously manifests itself in a preferably long lasting fragrant effect and/or biocidal effect of the substrate. This improved affinity lends a significant advantage to an inventive agent, as it is now ensured that on using the agent on a substrate, the probability is increased that larger amounts of the inventive oligomers, polymers or copolymers will be fixed on the substrate surface and will also remain adhered. The efficiency of the substrate fragrance or a biocidal efficiency will also be strongly increased.

It is particularly advantageous to now be able to provide agents that show an improved biocidal action. Here, the term "biocidal action" includes the usual fields of application of biocides, i.e. beginning from a broad action for conservation purposes up to a direct germ killing action of the biocide, for example on the use of an agent in textile treatment; in the context of the invention the deciding factor for the term "biocidal activity" is the ability to at least inhibit germ growth. The improvement in the biocidal action is due in retrospect to a long lasting release of the relevant biocide, as well as an increased affinity of the biocide carrier, for example a silicone derivative, to a correspondingly treated substrate. The efficiency of the biocide is therefore increased. Moreover, the biocide can be continuously released over a longer period, thus making possible a particularly long lasting biocidal action.

The inventive advantages of the long lasting release and improved affinity result, as the applicant was able to show, in the same way for fragrance alcohols, esters, ketones, aldehydes as for biocidal alcohols, esters, ketones, aldehydes. The term biocidal alcohol, i.e. compounds that have at least one alcohol group and at least inhibit germ growth, also encompasses alcohols that act as fragrance alcohols. These are particularly citronellol, eugenol, farnesol, thymol and geraniol. As a result of their difunctional character, these and similar biocidal fragrances are particularly advantageous. Additional biocidal alcohols are phenoxyethanol, 1,2-propylene glycol, glycerol, citric acid and its esters, lactic acid and its esters, salicylic acid and its esters, 2-benzyl-4-chlorophenol and 2,2'-methylene-bis-(6-bromo-4-chlorophenol). In the context of this invention, the lower alcohols, specifically methyl-, ethyl-n-propyl-, iso-propyl-, n-butyl-, iso-butyl- and tert-butyl alcohol are not considered to be biocidal alcohols. On the other hand, according to the invention, classical biocides with alcohol functions are expressly considered to be biocide alcohols, even if their action is attributed to other functional groups. Examples of these are various bromophenols and biphenylols as well as quaternary ammonium compounds having at least one long chain alkyl group and at least one alkyl group that carries a hydroxyl group.

In a particular embodiment, the inventive agents are characterized in that the inventive oligomers, polymers or copolymers comprise biocide alkoxy groups that are each, independently of each other, derived from the corresponding biocide alcohols. In this way, both individual biocide alcohols and also mixtures of biocide alcohols and also fragrance alcohol mixtures and biocide alcohol mixtures can be added.

Similarly and likewise preferred, esters, ketones and/or aldehydes with biocidal action in the above sense can be added, wherein, of course, the fragrance esters, ketones and/or aldehydes can also possess a concomitant biocidal action. Classical biocides that possess an ester, ketone or aldehyde function are considered to be biocide esters ketones or aldehydes, even if their action is attributed to other functional groups. Both individual biocide aldehydes, ketones, esters as well as corresponding mixtures and also corresponding fragrance aldehydes, ketones, esters and biocide aldehyde, ketone and ester mixtures can be added.

In a further preferred embodiment, the inventive agents comprise the inventive oligomer, polymer or copolymer, preferably the corresponding silicone derivatives, in amounts greater than 0.001 wt. %, preferably 0.002 to 10 wt. %, particularly from 0.01 to 5 wt. %, particularly preferably from 0.02 to 3 wt. % and quite particularly in quantities of 0.05 to 2 wt. %, in each case based on the total agent.

The exact quantities depend particularly on the field of application of each agent.

Thus, for the biocide-containing oligomers, polymers or copolymers, it is of interest to know if the biocides should only develop a conserving action for the agent or if they should have a germ-killing action during usage. There is no problem for the biocide expert to find the appropriate dose for the particular application.

If the biocides are intended to be added for conservation purposes, then the use of the inventive oligomers, polymers or copolymers is particularly advantageous, as the slow hydrolysis that preferably occurs under the influence of humidity causes a constant release of the biocide component in small quantities over a long period of time. Thus, for example, the long-term conservation of skin cream is effected with exceptionally low dosages of biocide. However, for uses in detergents, the germ killing action of biocides can also be the primary concern. In this case, the same amount of added biocide results in an increased activity, due to the good absorption of the inventive oligomers, polymers or copolymers.

In a preferred embodiment, the inventive agent comprises at least one silicone oligomer, polymer or copolymer, which on hydrolysis releases a fragrant and/or biocidal alcohol, aldehyde, ketone or ester, preferably included by the prior reaction with an olefinic silane.

Thus, as an example, an inventive silicone polymer is obtained from the following reaction of a siloxane with an olefinic silane that carries the fragrance.

2Ph(CH$_2$)$_2$O—Si(Me)$_2$—CH=CH$_2$+H—
[Si(Me$_2$)O]$_{25}$—H→Ph(CH$_2$)$_2$O—Si(Me)$_2$—
(CH$_2$)$_2$—Si(Me$_2$)O—[Si(Me$_2$)O]$_{23}$—Si(Me$_2$)—
(CH$_2$)$_2$—Si(Me)$_2$—O(CH$_2$)$_2$Ph

On hydrolysis of the reaction product selected as the example, Ph(CH$_2$)$_2$OH is released.

A preferred agent is an olefinic silane that is a reaction product of a fragrant and/or biocidal alcohol, aldehyde, ketone or ester with an olefinic halosilane or olefinic silicone alkoxide.

Thus, to give an example, an inventive olefinic silane can be obtained by treating phenylethyl alcohol with an appropriate halosilane or olefinic silicone alkoxide, for example:

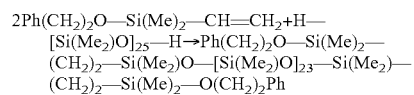
Ph(CH$_2$)$_2$OH+CH$_2$=CH—Si(Me)$_2$Cl→Ph(CH$_2$)$_2$O—Si(Me)$_2$—CH=CH$_2$+HCl or for example

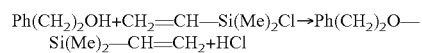
2Ph(CH$_2$)$_2$OH+CH$_2$=CH—Si(Me)Cl$_2$→
{Ph(CH$_2$)$_2$O}$_2$Si(Me)—CH=CH$_2$+2HCl In a preferred embodiment, the olefinic silane corresponds to Formula (2)

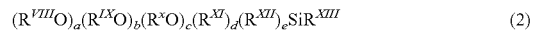
$(R^{VIII}O)_a(R^{IX}O)_b(R^XO)_c(R^{XI})_d(R^{XII})_e SiR^{XIII}$     (2)

wherein $R^{VIII}O$, $R^{IX}O$ and $R^{X}O$, each independently of one another, represent fragrance alkoxy groups, which derive from the corresponding fragrance alcohols $R^{VIII}OH$, $R^{IX}OH$ and $R^{X}OH$, wherein $R^{XI}$, $R^{XII}$ are selected from the group of monovalent $C_{1-40}$ hydrocarbon groups and monovalent $C_{1-40}$ alkoxy groups that can be aliphatic or aromatic, linear or branched, saturated or unsaturated, substituted or unsubstituted and can comprise heteroatoms such as oxygen, nitrogen, sulfur or halogens or others. Preferred $R^{II}$, $R^{III}$ groups are alkyl and/or alkoxy groups.

$R^{XIII}$ is a $C_{2-40}$ monovalent unsaturated hydrocarbon group with an olefinic end group, wherein a is 1-3, b, c, d, e are 0-2, with the proviso that a+b+c+d+e=3 and a, b, c, d, e are whole numbers.

A typical example (d) of such a compound according to Formula (2) is e.g.:

$$Ph(CH_2)_2O—Si(Me)_2—CH=CH_2 \quad (d)$$

In a further preferred embodiment, the olefinic silane corresponds to Formula (3):

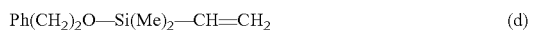

$$(R^{XIV})_a(R^{XV})_b(R^{XVI})_c(R^{XI})_d(R^{XII})_e SiR^{XIII} \quad (3)$$

wherein $R^{XIV}$, $R^{XV}$ und $R^{XVI}$ each independently of one another, have the Formula (4)

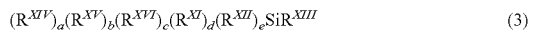

$$R^{XVII}(R^{XVIII})C=C(O—)—R^{XIX} \quad (4),$$

wherein $R^{XVII}$, $R^{XVIII}$ und $R^{XIX}$ independently of one another are chosen for each $R^{XIV}$, $R^{XV}$ and $R^{XVI}$ and wherein $R^{XI}$, $R^{XII}$ are selected from the group of monovalent $C_{1-40}$ hydrocarbon groups and monovalent $C_{1-40}$ alkoxy groups that can each be aliphatic or aromatic, linear or branched, saturated or unsaturated, substituted or unsubstituted and can comprise heteroatoms such as oxygen, nitrogen, sulfur or halogens or others. Preferred $R^{II}$, $R^{III}$ groups are alkyl and/or alkoxy groups.

$R^{XIII}$ is a $C_{2-40}$ monovalent unsaturated hydrocarbon group with an olefinic end group, wherein a is 1-3, b, c, d, e are 0-2, with the limitation that a+b+c+d+e=3 and a, b, c, d, e are whole numbers, and wherein $R^{XVII}$, $R^{XVIII}$ und $R^{XIX}$ are selected from the group consisting of hydrogen and monovalent $C_{1-100}$ hydrocarbon groups that can be aliphatic or aromatic, linear or branched, saturated or unsaturated, substituted or unsubstituted and can comprise heteroatoms such as oxygen, nitrogen, sulfur or halogens or others. It should be noted that the structure,

$$R^{XVII}(R^{XVIII})C=C(O—)—R^{XIX} \quad (4),$$

is a conjugated structure corresponding to the following enol structure, $$R^{XVII}(R^{XVIII})C=C(OH)—R^{XIX} \quad (4a),$$

that has one more hydrogen atom.

In the structure $R^{XVII}(R^{XVIII})C=C(O—)—R^{XIX}$ (4), the hyphen after the oxygen atom formally symbolizes a group, through which the whole structural element is bonded as the substituent to the relevant olefinic silane.

An example (e) of an inventive compound, obeying the Formula $(R^{XIV})_a(R^{XVIII})_b(R^{XVI})_c(R^{XI})_d(R^{XII})_e SiR^{XIII}$ (3), is consequently e.g. the following substance:

$$Me—(CH_2)_3—CH=CH—O—Si(Me)_2—CH=CH_2 \quad (e).$$

In this example, $R^{XVII}(R^{XVIII})C=C(O—)—R^{XIX}$ (4) corresponds to the following structure:

$$Me—(CH_2)_3—CH=C(O—)—H.$$

The Formula $R^{XVI}(R^{XVIII})C=C(O—)—R^{XIX}$ (4), can derive from any enolizable substance having a keto-function, particularly ketones, aldehydes and esters.

In a preferred embodiment the agent is characterized in that $R^{XIV}$, $R^{XV}$ and $R^{XVI}$ each independently of one another, possess the Formula $R^{XVII}(R^{XVIII})C=C(O—)—R^{XIX}$ (4) and derive from the group of the following aldehydes, ketones or esters, which is selected from 3-methyl-3(3-(1-methylethylphenyl))propanal), 2-methyl-3-(4-t-butylphenyl)propanal, 3-phenylpropional, 2-phenylpropional, propional, isobutyral, 2-methylbutyral, hexanal, octanal, nonanal, decanal, 3,7-dimethyl-1-al, p-tolylacetaldehyde, phenylacetaldehyde, 4-(3)(4-methyl-3-pentenyl)-3-cyclohexene-carbaldehyde, 2,6-dimethyl-5-heptenal, 3,7-dimethyl-2,6-octadienal, trans-4-decenal, cyclamenaldehyde, 4-(p-methoxyphenyl)-2-butanone, acetophenone, 2-pentanone, 2-butanone, 2-heptanone, 3-heptanone, 2-decanone, 3-penten-2-one, 6-methyl-5-hepten-2-on, geranyl acetone, 5-methyl-alpha-ionone, 2-acetonaphtone, 2-methyl-3-phenylpropan-2-yl acetate, linalyl acetate, menthanyl acetate, 2-phenylethyl acetate, tetrahydrolinalyl acetate, phenethyl propionate, phenethyl hexanoate, butyl acetate, phenoxyethyl isobutyrate, p-tert.-butylcyclohexyl acetate, linalyl acetate, dimethylbenzylcarbinyl acetate (DMBCA), phenylethyl acetate, benzyl acetate, ethylmethylphenyl glycinate, allylcyclohexyl propionate, styrallyl propionate, benzyl salicylate, cyclohexyl salicylate, floramate, melusate and jasmacyclate, linear alkanals with 8-18 carbon atoms, citral, citronellal, citronellyloxy-acetaldehyde, cyclamenaldehyde, lilial and bourgeonal, the ionones, α-isomethylionone and methyl cedryl ketone.

In a further preferred embodiment, the fragrance alkoxy groups and/or biocide alkoxy groups $R^{VIII}O$, $R^{IX}O$ and $R^{X}O$ are each derived from fragrance alcohols and/or biocide alcohols, selected from the group 2-methylbutanol, 3-pentanol, n-pentanol, 2-pentanol, n-hexanol, 2-methylpentanol, 1-decanol, sandela, nonadol, dimetol, thymol, 1-heptanol, menthol, eugenol, vanillin, o-vanillin, 4-(p-hydroxyphenyl)-2-butanone, syringealdehyde, prenol, cis-3-hexanol, trans-3-hexanol, cis-4-heptenol, trans-2-octenol, trans-2-cis-6-nonadienol, geraniol, nerol, ebanol, citronellol, crotyl alcohol, oleyl alcohol, linalool, α-terpineol, β-phenethyl alcohol, cinnamyl alcohol, benzyl alcohol, α-methylbenzyl alcohol, nonyl alcohol, 1-octanol, 3-octanol, phenethyl salicylate, hydrocinnamyl alcohol, cis-6-nonen-1-ol, trans-2-nonen-1-ol, methyl salicylate, cis-3-octenol, anisyl alcohol, carvacrol, dihydrocarveol, benzyl salicylate, tetrahydrogeraniol, ethyl salicylate, ethyl vanillin, isoeugenol, isopulegol, lauryl alcohol, tetrahydrolinalool, 2-phenoxyethanol, citronellol, eugenol, farnesol, thymol and geraniol. Compounds of this type are described, for example, in the EP 0 799 885, EP 0 771 785, WO 96/38528, U.S. Pat. No. 5,958,870.

In a further preferred embodiment, the molecular weight of the oligomers, polymers or copolymers that are comprised in the inventive agents is up to about 300,000, preferably up to 100,000, but particularly preferably in the range from about 150 to about 30,000. These molecular weights are advantageous because they result in a particularly advantageously lengthened fragrance release and/or biocide release, together with an overall advantageous affinity of the oligomer, polymer and/or copolymer to a substrate that has been treated with an inventive agent.

In a preferred embodiment, the content of the fragrance group or biocide group in the total weight of the oligomer, polymer or copolymer is up to 80 wt. %, preferably up to 70 wt. %, particularly between 0.001 and 60 wt. %, each based on the total agent.

According to a further preferred embodiment, the oligomer, polymer or copolymer is essentially unbranched, preferably at least 50%, advantageously at least 60%, in particular at least 70% linear.

In a further preferred embodiment, the oligomer, polymer or copolymer comprised in the inventive agent complies with the following Formula

with M: $R^{XX}R^{XXI}R^{XXII}SiO_{1/2}$; $M^F$: $R^{XX}R^{XXI}R^FSiO_{1/2}$; D: $R^{XXIII}R^{XXIV}SiO_{2/2}$; $D^F$: $R^{XXIII}R^FSiO_{2/2}$;
T: $R^{XXV}SiO_{3/2}$; $T^F$: $R^FSiO_{3/2}$ Q: $SiO_{4/2}$ wherein
$R^{XX}$, $R^{XXI}$, $R^{XXII}$, $R^{XXIII}$, $R^{XXIV}$, $R^{XXV}$ each independently of one another, are selected for each M,
$M^F$, D, $D^F$, T and $T^F$, from the group of $C_{1-40}$ monovalent, straight chain or branched, saturated or unsaturated alkyl or alkoxy groups or from the group of $C_{1-40}$ monovalent aryl or aryloxy groups. The above alkyl, alkoxy, aryl, aryloxy groups can be substituted or unsubstituted and can comprise heteroatoms such as oxygen, nitrogen, sulfur or halogen or others.

The letters f, g are positive numbers, h, i, j, k, l are positive numbers or equal to zero, wherein at least one of the h, i, j, k, l is not equal to zero and wherein at least one of g, i, or k is one or greater than one; and wherein $R^F$ is derived from one of the abovementioned and above described groups $(R^{VIII}O)_a(R^{IX}O)_b(R^XO)_c(R^{XI})_d(R^{XII})_eSiR^{XIII}$ (2) and/or $(R^{XIV})_a(R^{XV})_b(R^{XVI})_c(R^{XI})_d(R^{XII})_eSiR^{XIII}$ (3) wherein this group $R^F$ is bonded to a Si atom of the oligomer, polymer or copolymer through a divalent $C_{2-40}$ hydrocarbon bridging group derived from $R^{XIII}$ (a $C_{2-40}$ monovalent, unsaturated hydrocarbon group with an olefinic end group). In $R^F$, the olefinic end group is consequently no longer present. This is the only difference from the abovementioned and above described groups $(R^{VIII}O)_a(R^{IX}O)_b(R^XO)_c(R^{XI})_d(R^{XII})_eSiR^{XIII}$ (2)

and/or $(R^{XIV})_a(R_{XV})_b(R^{XVI})_c(R^{XI})_d(R^{XII})_eSiR^{XIII}$ (3).

In a further preferred embodiment, the oligomer, polymer or copolymer comprised in the inventive agent is selected from the following Formulae (6) and/or (7):

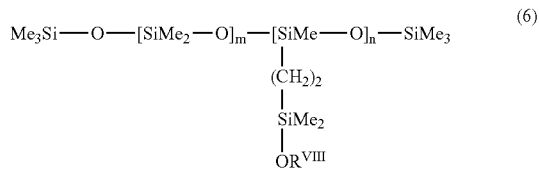

wherein $OR^{VIII}$ stands for a fragrance alkoxy group or biocide alkoxy group, particularly for a phenylethyl alcohol group. The letters m and n each have a positive value, with the limitation that the resulting silicone reaches a molecular weight of at least about 150.

or

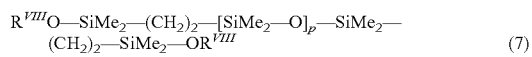

wherein $OR^{VIII}$ stands for a fragrance alkoxy group or biocide alkoxy group, particularly for a phenylethyl alcohol group, and wherein p has a positive value, with the limitation that the resulting silicone reaches a molecular weight of at least about 150.

The compound that preferably carries at least one cationic charge and is absorbed on hard and/or soft surfaces of substrates is preferably comprised in amounts of greater than 0.01 wt. %, advantageously in quantities of 0.02 to 45 wt. %, particularly from 5 to 40 wt. %, particularly advantageously from 10-35 wt. %, in each case based on the total weight of the agent.

There are specific compounds that are absorbed on hard and/or soft surfaces of substrates, which in aqueous media only temporarily carry a positive charge, particularly when the medium has a specific pH range. For example, below defined pH-values certain nitrogen-containing compounds are protonated in aqueous media and only then possess a positive charge.

In a further preferred embodiment, the inventive agent is therefore characterized in that the compound that is absorbed on hard and/or soft surfaces of substrates, is a compound that in aqueous media at pH-values below 4, preferably below 5, advantageously below 6, particularly advantageously below 7, quite particularly advantageously below 8, most advantageously below 9, especially below 10, possesses at least one cationic charge, the pH being measured at 20° C.

In a further preferred embodiment, the compound that preferably carries at least one cationic charge and is absorbed on hard and/or soft surfaces of substrates and is comprised in the inventive agent, is a compound that is selected from the group of cationic or amphoteric emulsifiers, cationic surfactants, zwitterionic compounds, ampholytes, amphosurfactants, betaines and/or cationic or amphoteric polymers.

In a preferred embodiment, the compound that preferably carries at least one cationic charge and is absorbed on hard and/or soft surfaces of substrates, is a cationic surfactant, preferably a quaternary ammonium compound, advantageously an alkylated quaternary ammonium compound, in which at least one alkyl chain is interrupted by an ester group and/or amido group. The advantage of these substances resides in the fact that they not only improve the affinity of the oligomer, polymer and/or copolymer for a substrate, but after an appropriate treatment of the substrate, also lend a pleasant feel to said substrate.

Suitable examples are quaternary ammonium compounds of Formulas (8) and (9),

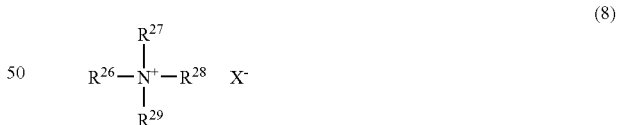

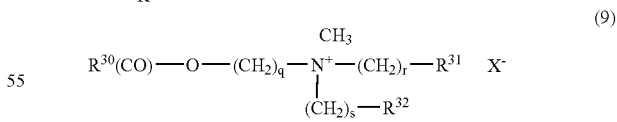

wherein in (8) $R^{26}$ and $R^{27}$ stand for an acyclic alkyl group having 12 to 24 carbon atoms, $R^{28}$ stands for a saturated $C_1$-$C_4$ alkyl or hydroxyalkyl group, $R^{29}$ is either equal to $R^{26}$, $R^{27}$ or $R^{28}$ or stands for an aromatic group. $X^-$ stands either for a halide ion, methosulfate ion, methophosphate ion or phosphate ion as well as their mixtures. Exemplary cationic compounds of Formula (8) are didecyl dimethyl ammonium chloride, ditallow dimethyl ammonium chloride or dihexadecyl ammonium chloride.

Compounds of Formula (9) are so-called esterquats. Esterquats are characterized by their outstanding biodegradability. Here, $R^{30}$ stands for an aliphatic alkyl group with 12 to 22 carbon atoms and 0, 1, 2 or 3 double bonds, $R^{31}$ stands for H, OH or $O(CO)R^a$, $R^{32}$ independently of $R^{31}$ stands for H, OH or $O(CO)R^b$, wherein $R^a$ and $R^b$, independently of each other, each stand for an aliphatic alkyl group having 12 to 22 carbon atoms with 0, 1, 2 or 3 double bonds, q, r and s independently of each other can each have the value 1, 2 or 3. $X^-$ can be either a halide ion, methosulfate ion, methophosphate ion or phosphate ion as well as their mixtures.

In a preferred embodiment, the inventive agent is characterized in that the compound that is absorbed on hard and/or soft surfaces of substrates is a quaternary ammonium compound selected from the abovementioned Formula (9).

Preferred compounds comprise a group $O(CO)R^a$ for $R^{31}$ and alkyl groups with 16 to 18 carbon atoms for $R^{30}$ and $R^a$. Particularly preferred are compounds in which $R^{32}$ stands moreover for OH. Examples of compounds of Formula (II) are methyl-N-(2-hydroxyethyl)-N,N-di(tallowacyloxyethyl) ammonium methosulfate, bis(palmitoyl)ethyl hydroxyethyl methyl ammonium methosulfate or methyl-N,N-bis(acyloxyethyl)-N-(2-hydroxyethyl) ammonium methosulfate. When quaternized compounds of Formula (II) are used that have unsaturated groups, the acyl groups are preferred, whose corresponding fatty acids have an iodine number between 5 and 80, preferably between 10 and 60 and particularly between 15 and 45 and which have a cis/trans isomer ratio (in wt. %) of greater than 30:70, preferably greater than 50:50 and particularly greater than 70:30. Commercial examples are the methylhydroxyalkyl-dialkoyloxyalkylammonium methosulfates marketed by Stepan under the trade name Stepantex® or known products from Cognis with the trade name Dehyquart® or the known products manufactured by Goldschmidt-Witco under the name Rewoquat®. Further preferred compounds are the diesterquats of Formula (10), which are available under the names Rewoquat® W 222 LM or CR 3099. The particular advantage of the esterquats results from the fact that they not only afford a good fixation of the silicone derivative to the substrate, but also simultaneously— when the treated substrates are textiles or fibers—enhance their softness and improve their feel.

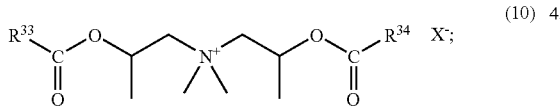

(10)

$R^{33}$ und $R^{34}$ stand, independently of each other, each for an aliphatic group having 12 to 22 carbon atoms with 0, 1, 2 or 3 double bonds.

Besides the above described cationic compounds, other known cationic compounds can also be used, such as, for example quaternary imidazolinium compounds of Formula (11),

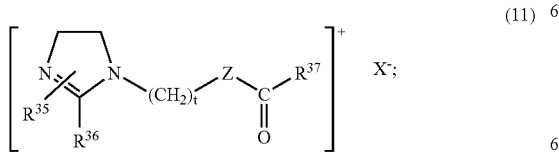

(11)

wherein $R^{35}$ stands for a saturated alkyl group with 1 to 4 carbon atoms, $R^{36}$ and $R^{37}$, independently of each other, each stand for an aliphatic, saturated or unsaturated alkyl group with 12 to 18 carbon atoms, $R^{36}$ can alternatively stand for $O(CO)R^c$, wherein $R^c$ means an aliphatic, saturated or unsaturated alkyl group with 12 to 18 carbon atoms, and Z means an NH group or oxygen and $X^-$ is an anion, t can take values between 1 and 4.

Additional preferred quaternary, cationic compounds are described using Formula (12),

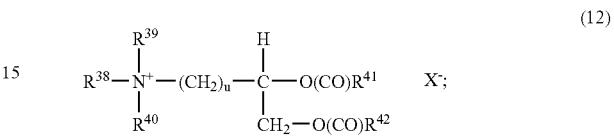

(12)

wherein $R^{38}$, $R^{39}$ and $R^{40}$ independently of one another stand for a $C_{1-4}$ alkyl, alkenyl or hydroxyalkyl group, $R^{41}$ and $R^{42}$, each independently selected, represents a $C_{8-28}$ alkyl group and u is a number between 0 and 5. $X^-$ is a suitable anion, preferably a halide ion, methosulfate ion, methophosphate ion or phosphate ion as well as their mixtures.

In a preferred embodiment, the compound that is absorbed on hard and/or soft surfaces of substrates and comprised in the inventive agent is a quaternary ammonium compound selected from the abovementioned Formula (12).

Besides the compounds of Formulae (8) and (9), short chain, water-soluble, quaternary ammonium compounds can also be employed, such as trihydroxyethyl methyl ammonium methosulfate or the alkyl trimethyl ammonium chlorides, dialkyl dimethyl ammonium chlorides and trialkyl methyl ammonium chlorides, e.g. cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride.

Protonated alkylamine compounds that exhibit a softening action, as well as the non-quaternary, protonated precursors of the cationic emulsifiers are also suitable.

Quaternized protein hydrolyzates represent additional compounds that are absorbed on hard and/or soft surfaces of substrates and can be used according to the invention.

Compounds of Formula (13) are likewise usable,

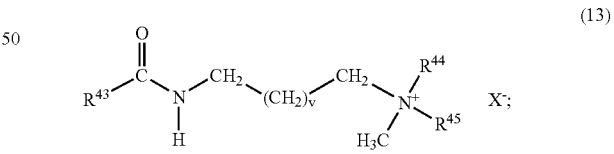

(13)

which can be alkylamido amines in their non-quaternary form or, as shown, in their quaternary form. $R^{43}$ can be an aliphatic alkyl group having 12 to 22 carbon atoms with 0, 1, 2 or 3 double bonds, v can assume values between 0 and 5. $R^{44}$ and $R^{45}$ stand, independently of one another, each for H, $C_{1-4}$ alkyl or hydroxyalkyl. Preferred compounds are fatty acid amido amines such as stearylamidopropyl dimethylamine, available under the trade name Tego Amid®S 18 or 3-tallowamidopropyl trimethyl ammonium methosulfate, available under the trade name Stepantex® X 9124, which are characterized by their good conditioning action as well as by their color transfer inhibiting action and particularly by their good biodegradability. Alkylated quaternary ammonium compounds having at least one alkyl chain interrupted by an ester group and/or an amido group, particularly N-methyl-N(2-hydroxyethyl)-N,N-(ditallowacyloxyethyl) ammonium methosulfate and/or N-methyl-N(2-hydroxyethyl)-N,N-(palmitoyloxyethyl) ammonium methosulfate are particularly preferred.

In a preferred embodiment, the compound that preferably carries at least one cationic charge and is absorbed on hard and/or soft surfaces of substrates is a cationic nitrile of the following Formula (14)

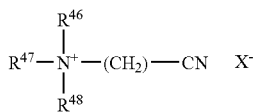
(14)

in which $R^{46}$ stands for —H, —$CH_3$, a $C_{2-24}$ alkyl or alkenyl group, a substituted $C_{2-24}$ alkyl or alkenyl group having at least one substituent from the group of —Cl, —Br, —OH, —$NH_2$, —CN, an alkyl or alkenylaryl radical having a $C_{1-24}$ alkyl group or for a substituted alkyl or alkenylaryl group having a $C_{1-24}$ alkyl group and at least a further substituent on the aromatic ring, $R^{47}$ and $R^{48}$, independently of one another are selected from —$CH_2$—CN, —$CH_3$, —$CH_2$—$CH_3$, —$CH_2$—$CH_2$—$CH_3$, —$CH(CH_3)$—$CH_3$, —$CH_2$—OH, —$CH_2$—$CH_2$—OH, —CH(OH)—$CH_3$, —$CH_2$—$CH_2$—$CH_2$—OH, —$CH_2$—CH(OH)—$CH_3$, —CH(OH)—$CH_2$—$CH_3$, —$(CH_2CH_2$—$O)_n$H with n=1, 2, 3, 4, 5 or 6 and X is an anion.

The general Formula (14) includes a large number of cationic nitriles that are all usable in the context of the present invention. The inventive agents comprise with particular advantage cationic nitriles, in which $R^{46}$ stands for methyl, ethyl, propyl, isopropyl or an n-butyl, n-hexyl, n-octyl, n-decyl, n-dodecyl, n-tetradecyl, n-hexadecyl or n-octadecyl group. $R^{47}$ and $R^{48}$ are advantageously selected from methyl, ethyl, propyl, isopropyl and hydroxyethyl, wherein one or both groups can be advantageously also a cyanomethyl group.

For reasons of easier synthesis, compounds are preferred, in which the groups $R^{46}$ to $R^{48}$ are identical, for example $(CH_3)_3N^+CH_2$—CN $X^-$, $(CH_3CH_2)_3N^+CH_2$—CN $X^-$, $(CH_3CH_2CH_2)_3N^+CH_2$—CN $X^-$, $(CH_3CH(CH_3))_3N^+CH_2$—CN $X^-$, or $(HOCH_2$—$CH_2)_3N^+CH_2$—CN $X^-$. A preferred subject of the present application is accordingly an inventive agent comprising a cationic nitrile according to the following Formula (15)

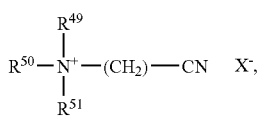
(15)

in which $R^{49}$, $R^{50}$ and $R^{51}$ independently of one another are selected from —$CH_3$, —$CH_2$—$CH_3$, —$CH_2$—$CH_2$—$CH_3$, —$CH(CH_3)$—$CH_3$, wherein $R^{49}$ can also be —H and X is an anion, wherein preferably $R^{50}$=$R^{51}$=—$CH_3$ and in particular $R^{49}$=$R^{50}$=$R^{51}$=—$CH_3$ and compounds of the formulae $(CH_3)_3N^{(+)}CH_2$—CN $X^-$, $(CH_3CH_2)_3N^{(+)}CH_2$—CN $X^-$, $(CH_3CH_2CH_2)_3N^{(+)}CH_2$—CN $X^-$, $(CH_3CH(CH_3))_3N^{(+)}CH_2$—CN $X^-$, or $(HO$—$CH_2$—$CH_2)_3N^{(+)}CH_2$—CN $X^-$ are particularly preferred.

Inventive agents that comprise a cationic nitrile of both abovementioned formulae, preferably the latter formula, particularly preferably the formula $(CH_3)_3N^{(+)}CH_2$—CN $X^-$, in which $X^-$ stands for an anion that is selected from the group chloride, bromide, iodide, hydrogen sulfate, methosulfate, lauryl sulfate, dodecylbenzene sulfonate, p-toluene sulfonate (tosylate), cumene sulfonate or xylene sulfonate or mixtures thereof, are particularly preferred.

Of course, an inventive agent can comprise a plurality of cationic nitriles of the above-described structure. Industrially achievable and preferred in the context of the present application are agents, which comprise two, three, four or five different cationic nitriles.

A particular advantage from the incorporation of the inventive nitrilequat results from its function as a bleach activator.

The content by weight of the cationic nitrile to the total weight of the inventive agent can vary; the content by weight of the cationic nitrile can be up to 60 wt. %. In the context of the present application, however, those inventive agents are preferred, which have a content by weight of cationic nitrile of 0.01 to 40 wt. %, advantageously 0.1 to 32 wt. %, preferably 0.2 to 28 wt. %, particularly preferably 0.5 to 24 wt. % and particularly 1.0 to 20 wt. %, each based on the total weight of the agent.

In a preferred embodiment, the compound that is absorbed on hard and/or soft surfaces of substrates is a polymer that preferably carries at least one cationic charge, particularly a cationic or amphoteric polymer, for example a cationic or amphoteric sugar derivative or starch derivative or a cationic or amphoteric cellulose derivative.

Suitable cationic polymers include the polyquaternium polymers such as those in the CTFA Cosmetic Ingredient Dictionary (The Cosmetic, Toiletry and Fragrance, Inc., 1997), particularly those polyquaternium-6, polyquaternium-7, polyquaternium-10 polymers also described as Merquats (Ucare Polymer IR 400; Amerchol), polyquaternium-4-copolymers, such as graft copolymers with a cellulosic backbone and quaternary ammonium groups that are bonded through allyl dimethyl ammonium chloride, cationic cellulose derivatives like cationic guar, such as guar hydroxypropyl triammonium chloride and similar quaternized guar derivatives (e.g. cosmedia guar, manufactured by Cognis GmbH), cationic quaternary sugar derivatives (cationic alkyl polyglucosides), e.g. the commercial product Glucquat® 100, according to CTFA nomenclature a "Lauryl Methyl Gluceth-10 Hydroxypropyl Dimonium Chloride", copolymers of PVP and dimethylamino methacrylate, copolymers of vinyl imidazole and vinyl pyrrolidone, aminosilicone polymers and copolymers.

Polyquaternized polymers (e.g. Luviquat Care from BASF) and also cationic biopolymers based on chitin and its derivatives, for example the polymer obtained under the trade name Chitosan® (manufacturer: Cognis) can also be employed.

Cationic silicone oils, such as, for example, the commercially available products Q2-7224 (manufacturer: Dow Corning; a stabilized trimethylsilylamodimethicone), Dow Corning® 929 emulsion (comprising a hydroxylamino-modified silicone, also referred to as amodimethicone), SM-2059 (manufacturer: General Electric), SLM-55067 (manufacturer: Wacker), and Abil®-Quat 3270 and 3272 (manufacturer: Goldschmidt-Rewo; diquaternary polydimethylsiloxanes, Quaternium-80), as well as siliconequat Rewoquat® SQ 1 (Tegopren® 6922, manufacturer: Goldschmidt-Rewo) are similarly suitable.

Particularly preferred cationic or amphoteric polymers comprise at least one ethylenically unsaturated monomer unit of the general Formula (16)

in which $R^{52}$ to $R^{55}$ independently of one another stand for —H, —$CH_3$, a linear or branched, saturated alkyl group containing 2 to 12 carbon atoms, a linear or branched, mono- or polyunsaturated alkenyl group containing 2 to 12 carbon atoms, with —$NH_2$, —OH or —COOH substituted alkyl or alkenyl groups as defined above, a heteroatomic group with at least one positively charged group, a quaternized nitrogen atom or at least one amine group with a positive charge between pH 2 and 11 or for —COOH or —COOR$^d$, wherein R$^d$ is a saturated or unsaturated, linear or branched hydrocarbon group containing 1 to 12 carbon atoms.

Exemplary cited (unpolymerized) monomer units are diallylamine, methyldiallylamine, dimethyl dimethyl ammonium salts, acrylamidopropyl trimethyl ammonium salts ($R^{52}$, $R^{53}$, and $R^{54}$, =H, $R^{55}$=C(O)NH($CH_2$)$_2$N$^+$($CH_3$)$_3$X$^-$), methacrylamidopropyl trimethyl ammonium salts ($R^{52}$ and $R^{53}$=H, $R^{54}$=$CH_3$ H, $R^{55}$=C(O)NH($CH_2$)$_2$N+($CH_3$)$_3$X$^-$).

Particularly preferred added constituents of the amphoteric polymers are unsaturated carboxylic acids of the general Formula (17)

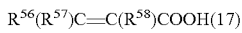

in which $R^{56}$ to $R^{58}$ independently of one another stand for —H, —$CH_3$, a linear or branched, saturated alkyl group containing 2 to 12 carbon atoms, a linear or branched, mono- or polyunsaturated alkenyl group containing 2 to 12 carbon atoms, with —$NH_2$, —OH or —COOH substituted alkyl or alkenyl groups as defined above or —COOH or —COOR$^e$, wherein R$^e$ is a saturated or unsaturated, linear or branched hydrocarbon group containing 1 to 12 carbon atoms.

Particularly preferred amphoteric polymers comprise monomer units derived from diallylamine, particularly dimethyl diallyl ammonium salts and/or methacrylamidopropyl trimethyl ammonium salts, preferably in the form of chlorides, bromides, iodides, hydroxides, phosphates, sulfates, hydrogen sulfates, ethyl sulfates, methyl sulfates, mesylates, tosylates, formates or acetates in combination with monomer units from the group of ethylenically unsaturated carboxylic acids.

In a further preferred embodiment, the compound that preferably carries at least one cationic charge and is absorbed on hard and/or soft surfaces of substrates is a zwitterionic compound. A zwitterionic compound is characterized in that both a positively charged group and a negatively charged group exist in the same molecule. The group of zwitterionic compounds also includes for example the betaines. In the strictest sense betaines are compounds that possess a moiety $R_3N^+$—$CH_2$—COO$^-$, however betaines in the wider sense can also include other zwitterionic compounds in which for example the positive charge is formally on the N or P atom and the negative charge is formally on the O, S, B or C atom.

In a further preferred embodiment, the compound that preferably carries at least one cationic charge and is absorbed on hard and/or soft surfaces of substrates is an ampholyte. Ampholytes are chemical compounds, which can ionize in aqueous media and thereby, depending on the pH of the medium, have an anionic or cationic character; advantageously ampholytes can both accept and also eliminate a proton, thus forming cations in acidic solution and anions in alkaline solution.

In a further preferred embodiment, the compound that preferably carries at least one cationic charge and is absorbed on hard and/or soft surfaces of substrates is a zwitterionic compound of the following Formula (18)

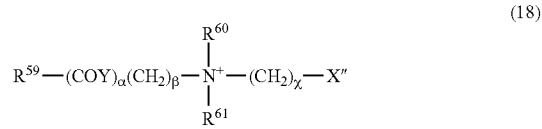

in which $R^{59}$ stands for a $C_{6-28}$-alkyl or alkenyl group, $R^{60}$ and $R^{61}$ are each independently of one another $C_{1-4}$ alkyl groups; a stands for the number 0 or 1, β and χ are each selected independently of one another from whole numbers from 1 to 4. Y is oxygen or nitrogen; X is a compatible anion.

It is preferably an alkylamidoalkylene carboxylic acid betaine having the following Formula (19):

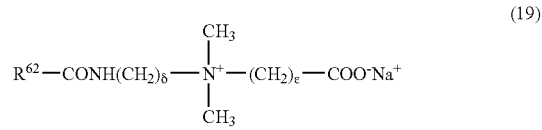

wherein δ and ε, independently of one another, are whole numbers from 1-4, advantageously b is equal to 2 or 3 and c equals 2 or 3 and $R^{62}$ stands for a $C_{10-18}$ alkyl chain or mixtures thereof.

In a preferred embodiment, the inventive agent is in solid, dispersed, powdered, granular or compressed form. If the agent is in compressed form, then it is particularly in the form of tablets, which consist of a single or a plurality of phases.

However, depending on the application of the agent, it can be required to be provided in liquid form.

In a preferred embodiment, the agent is thus a gel or in liquid form, particularly emulsified, wherein advantageously up to 95 wt. %, preferably 20 to 90 wt. %, further preferably 50-80 wt. % of one or a plurality of solvents is comprised.

However, from the industrial application point of view, one may wish to provide inventive, advantageously liquid agents that comprise little or no water. In a further preferred embodiment, the agent is accordingly in non-aqueous form. In the context of this invention, the term non-aqueous form is understood to mean water contents below 15 wt. %, based on the agent, preferably water contents below 10 wt. %, particularly preferably below 8 wt. %. Water contents lower than 6 wt. % are of particular importance; however, water contents between 2 and 0.001 wt. % based on the agent are particularly preferred.

The advantage of reducing the water content in the agent is that the ingredients of the agent can be added in concentrated form during the application and therefore the agents are better processable, for example emulsifiable.

The inventive liquid agent is advantageously a liquid detergent, liquid dish washing agent, cleaning gel, liquid textile treatment agent or liquid skin conditioner and/or hair cleaning- and/or conditioning agent.

The inventive agents can comprise, besides the inventive ingredients in the form of oligomers, polymers or copolymers and the compound that preferably carries at least one cationic charge and is absorbed on hard and/or soft surfaces of substrates, any ingredient and active material that are relevant to the specified use.

Accordingly, this presents no difficulty to an expert who has to select the additionally required ingredients.

Besides the cosmetic formulations for cleaning and care of the body, particular importance with regard to the inventive agent is to be attributed to the total complex of the washing and cleaning agent. Therefore, the following important ingredients, which can be additionally comprised in the inventive agents, are listed below, advantageously when these agents concern the total complex of the washing and cleaning agent. In principal, these agents can comprise all the substances that are relevant for a washing and cleaning agent. They include active materials such as surfactants (for example, anionic, non-ionic surfactants), builders (inorganic and organic builders), bleaching-agents (such as for example peroxy bleaching-agents and chlorine bleaching-agents), bleach activators, bleach stabilizers, bleach catalysts, enzymes, special polymers (for example those with cobuilder properties), and anti-graying inhibitors. Washing auxiliaries and cleaning auxiliaries can also be comprised. Examples of these are optical brighteners, UV-stabilizers as well as soil repellents, i.e. polymers that counteract redeposition of dirt on the fibers or on the hard surfaces. In addition, the inventive agent can comprise one or more typical auxiliaries and additives, particularly selected from the group of electrolytes, colorants, perfumes, fragrances, perfume carriers, pH adjustors, complexing agents, fluorescence agents, foam inhibitors, anti-graying inhibitors, anti-creasing agents, antioxidants, antistatics, ironing auxiliaries, UV-absorbers, antiredeposition agents, germicides, antimicrobials, fungicides, viscosity regulators, pearlizers, color-transfer inhibitors, anti-shrinkage agents, corrosion inhibitors, conservation agents, softeners, softening rinse agents, protein hydrolyzates, water-proofing and impregnation agents, non-aqueous solvents, hydrotropes, silicone oils as well as swelling and non-slip agents as well as quaternary ammonium compounds optionally containing ester bonds.

Exemplary suitable anionic surfactants are those of the sulfonate and sulfate type. Suitable surfactants of the sulfonate type are, advantageously $C_{9-13}$ alkylbenzene sulfonates, olefin sulfonates, i.e. mixtures of alkene- and hydroxyalkane sulfonates, and disulfonates, as are obtained, for example, from $C_{12-18}$ monoolefins having a terminal or internal double bond, by sulfonation with gaseous sulfur trioxide and subsequent alkaline or acidic hydrolysis of the sulfonation products. Alkane sulfonates are also suitable, which are obtained from $C_{12-18}$ alkanes by sulfochlorination or sulfoxidation, for example, with subsequent hydrolysis or neutralization. The esters of sulfofatty acids (ester sulfonates), e.g. the sulfonated methyl esters of hydrogenated coco-, palm nut- or tallow fatty acids are likewise suitable.

Further suitable anionic surfactants are sulfated fatty acid esters of glycerine. They include the mono-, di- and triesters and also mixtures of them, such as those obtained by the esterification of a monoglycerin with 1 to 3 moles fatty acid or the transesterification of triglycerides with 0.3 to 2 moles glycerol. Preferred sulfated fatty. acid esters of glycerol in this case are the sulfated products of saturated fatty acids with 6 to 22 carbon atoms, for example caproic acid, caprylic acid, capric acid, myristic acid, lauric acid, palmitic acid, stearic acid or behenic acid.

Preferred alk(en)yl sulfates are the alkali and especially sodium salts of the sulfuric acid half-ester derived from the $C_{12}$-$C_{18}$ fatty alcohols, for example from coconut butter alcohol, tallow alcohol, lauryl, myristyl, cetyl or stearyl alcohol or from $C_{10}$-$C_{20}$ oxo alcohols and those half-esters of secondary alcohols of these chain lengths. Additionally preferred are alk(en)yl sulfates of the said chain lengths, which contain a synthetic, straight-chained alkyl group produced on a petrochemical basis, which show similar degradation behaviour to the suitable compounds based on fat chemical raw materials. The $C_{12}$-$C_{16}$alkyl sulfates and $C_{12}$-$C_{15}$ alkyl sulfates and $C_{14}$-$C_{15}$ alkyl sulfates are preferred on the grounds of laundry performance. The 2,3-alkyl sulfates, which are manufactured according to the U.S. Pat. Nos. 3,234,258 or 5,075,041, and which can be obtained from Shell Oil Company under the trade name DAN®, are also suitable anionic surfactants.

Sulfuric acid mono-esters derived from straight-chained or branched $C_{7-21}$ alcohols ethoxylated with 1 to 6 mols ethylene oxide are also suitable, for example 2-methyl-branched $C_{9-11}$ alcohols with an average of 3.5 mol ethylene oxide (EO) or $C_{12-18}$ fatty alcohols with 1 to 4 EO. Due to their high foaming performance, they are only used in fairly small quantities in cleaning agents, for example in amounts of 1 to 5% by weight.

Other suitable anionic surfactants are the salts of alkylsulfosuccinic acid, which are also referred to as sulfosuccinates or esters of sulfosuccinic acid and the monoesters and/or di-esters of sulfosuccinic acid with alcohols, preferably fatty alcohols and especially ethoxylated fatty alcohols. Preferred sulfosuccinates contain $C_{8-18}$ fatty alcohol groups or mixtures of them. Especially preferred sulfosuccinates contain a fatty alcohol group derived from the ethoxylated fatty alcohols that are under consideration as non-ionic surfactants. Once again the especially preferred sulfosuccinates are those, whose fatty alcohol residues are derived from ethoxylated fatty alcohols with narrow range distribution. It is also possible to use alk(en)ylsuccinic acid with preferably 8 to 18 carbon atoms in the alk(en)yl chain or its salts.

Soaps in particular can be considered as further anionic surfactants. Saturated fatty acid soaps are suitable, such as the salts of lauric acid, myristic acid, palmitic acid, stearic acid, hydrogenated erucic acid and behenic acid, and especially soap mixtures derived from natural fatty acids such as coconut oil fatty acid, palm kernel oil fatty acid or tallow fatty acid.

Anionic surfactants, including soaps may be in the form of their sodium, potassium or ammonium salts or as soluble salts of organic bases, such as mono-, di- or triethanolamine. Preferably, anionic surfactants are in the form of their sodium or potassium salts, especially sodium.

A further class of anionic surfactants is that of the ether carboxylic acids, obtainable by treating fatty alcohol ethoxylates with sodium chloroacetate in the presence of basic catalysts. They have the general Formula 20: $R^{63}$—($CH_2$—$CH_2$—O$)_f$—$CH_2$—COOH (20) with $R^{63}$ equal to $C_1$-$C_{18}$ and f equal to 0.1 to 20. The manufacture and application are, for example, described in Seifen, Öle, Fette, Wachse 101, 37 (1975); 115, 235 (1989) and Tenside Deterg. 25, 308 (1988).

Suitable anionic surfactants are also, for example, the partial esters of di or polyhydroxyalkanes, mono and disaccharides, polyethylene glycols with the ene adducts of maleic anhydride on at least mono-unsaturated carboxylic acids having a chain length of 10 to 25 carbon atoms with an acid number of 10 to 140, described in DE 38 08 114 A1 (Grillo-Werke) and EP 0 046 070 A (Grillo-Werke); reference to both patents is made in this context and their contents are hereby incorporated in this application.

Preferred anionic surfactants possess, in addition to a linear or branched, saturated or unsaturated, aliphatic or aromatic, acyclic or cyclic, optionally alkoxylated alkyl group with 4 to 28, preferably 6 to 20, particularly preferably 10 to 16, most preferably 12 to 14 carbon atoms, two or more anionic, particularly two acid groups, preferably carboxylate, sulfonate and/or sulfate groups, particularly a carboxylate and a sulfate group. Examples of these compounds are the sulfofatty acid salts, the acyl glutamates, the monoglyceride disulfates and the alkyl ethers of glycerine disulfate as well as particularly the monoesterified sulfosuccinates described below.

Particularly preferred anionic surfactants are the sulfosuccinates, sulfosuccinamates and sulfosuccinamides, particularly sulfosuccinates and sulfosuccinamates, most preferably sulfosuccinates. The sulfosuccinates are salts of the mono and diesters of sulfosuccinic acid $HOOCCH(SO_3H)CH_2COOH$, whereas the sulfosuccinamates are understood to mean the salts of the monoamide of sulfosuccinic acid and the sulfosuccinamides are the salts of the diamide of sulfosuccinic acid. A detailed description of these known anionic surfactants is given by A. Domsch and B. Irrgang in *Anionic surfactants: organic chemistry* (edited by H. W. Stache; Surfactant science series; volume 56; ISBN 0-8247-9394-3; Marcel Dekker, Inc., New York 1996, p. 501-549).

The salts are preferably alkali metal salts, ammonium salts as well as mono, di or trialkanolammonium salts, for example, mono, di or triethanolammonium salts, particularly lithium, sodium, potassium or ammonium salts, particularly preferably sodium or ammonium salts, most preferably sodium salts.

In the sulfosuccinates, one or both carboxylic groups of the sulfosuccinic acid are esterified, advantageously with one or two of the same or different linear or branched, saturated or unsaturated, acyclic or cyclic, optionally alkoxylated alcohols with 4 to 22, advantageously 6 to 20, particularly 8 to 18, particularly preferably 10 to 16, most preferably 12 to 14 carbon atoms. Particularly preferred esters are those of linear and/or saturated and/or acyclic and/or alkoxylated alcohols, particularly linear, saturated fatty alcohols and/or linear, saturated fatty alcohols alkoxylated with ethylene oxide and/or propylene oxide, advantageously ethylene oxide, with a degree of alkoxylation of 1 to 20, advantageously 1 to 15, particularly 1 to 10, particularly preferably 1 to 6, most preferably 1 to 4. In the context of the present invention, the monoesters are preferred over the diesters. A particularly preferred sulfosuccinate is the disodium salt of the lauryl polyglycol ester of sulfosuccinic acid (lauryl-EO-sulfosuccinate, di-Na salt; INCI disodium laureth sulfosuccinate), that, for example, is commercially available as Tego® Sulfosuccinat F 30 (Goldschmidt) with a sulfosuccinate content of 30 wt. %.

In the sulfosuccinates or sulfosuccinamides, one or both carboxylic groups of the sulfosuccinic acid form a carboxylic acid amide, advantageously with a primary or secondary amine that has one or two of the same or different linear or branched, saturated or unsaturated, acyclic or cyclic, optionally alkoxylated alkyl groups with 4 to 22, advantageously 6 to 20, particularly 8 to 18, particularly preferably 10 to 16, most preferably 12 to 14 carbon atoms. Linear and/or saturated and/or acyclic alkyl groups, particularly linear, saturated fatty alkyl groups, are preferred.

Further suitable sulfosuccinates and sulfosuccinamates according to INCI are for example the following that are described in more detail in the *International Cosmetic Ingredient Dictionary and Handbook*: Ammonium Dinonyl Sulfosuccinate, Ammonium Lauryl Sulfosuccinate, Diammonium Dimethicone Copolyol Sulfosuccinate, Diammonium Lauramido-MEA Sulfosuccinate, Diammonium Lauryl Sulfosuccinate, Diammonium Oleamido PEG-2 Sulfosuccinate, Diamyl Sodium Sulfosuccinate, Dicapryl Sodium Sulfosuccinate, Dicyclohexyl Sodium Sulfosuccinate, Diheptyl Sodium Sulfosuccinate, Dihexyl Sodium Sulfosuccinate, Diisobutyl Sodium Sulfosuccinate, Dioctyl Sodium Sulfosuccinate, Disodium Cetearyl Sulfosuccinate, Disodium Cocamido MEA-Sulfosuccinate, Disodium Cocamido MIPA-Sulfosuccinate, Disodium Cocamido PEG-3 Sulfosuccinate, Disodium Coco-Glucoside Sulfosuccinate, Disodium Cocoyl Butyl Gluceth-10 Sulfosuccinate, Disodium C12-15 Pareth Sulfosuccinate, Disodium Deceth-5 Sulfosuccinate, Disodium Deceth-6 Sulfosuccinate, Disodium Dihydroxyethyl Sulfosuccinylundecylenate, Disodium Dimethicone Copolyol Sulfosuccinate, Disodium Hydrogenated Cottonseed Glyceride Sulfosuccinate, Disodium Isodecyl Sulfosuccinate, Disodium Isostearamido MEA-Sulfosuccinate, Disodium Isostearamido MIPA-Sulfosuccinate, Disodium Isostearyl Sulfosuccinate, Disodium Laneth-5 Sulfosuccinate, Disodium Lauramido MEA-Sulfosuccinate, Disodium Lauramido PEG-2 Sulfosuccinate, Disodium Lauramido PEG-5 Sulfosuccinate, Disodium Laureth-6 Sulfosuccinate, Disodium Laureth-9 Sulfosuccinate, Disodium Laureth-12 Sulfosuccinate, Disodium Lauryl Sulfosuccinate, Disodium Myristamido MEA-Sulfosuccinate, Disodium Nonoxynol-10 Sulfosuccinate, Disodium Oleamido MEA-Sulfosuccinate, Disodium Oleamido MIPA-Sulfosuccinate, Disodium Oleamido PEG-2 Sulfosuccinate, Disodium Oleth-3 Sulfosuccinate, Disodium Oleyl Sulfosuccinate, Disodium Palmitamido PEG-2 Sulfosuccinate, Disodium Palmitoleamido PEG-2 Sulfosuccinate, Disodium PEG-4 Cocamido MIPA-Sulfosuccinate, Disodium PEG-5 Laurylcitrate Sulfosuccinate, Disodium PEG-8 Palm Glycerides Sulfosuccinate, Disodium Ricinoleamido MEA-Sulfosuccinate, Disodium Sitostereth-14 Sulfosuccinate, Disodium Stearamido MEA-Sulfosuccinate, Disodium Stearyl Sulfosuccinamate, Disodium Stearyl Sulfosuccinate, Disodium Tallamido MEA-Sulfosuccinate, Disodium Tallowamido MEA-Sulfosuccinate, Disodium Tallow Sulfosuccinamate, Disodium Tridecylsulfosuccinate, Disodium Undecylenamido MEA-Sulfosuccinate, Disodium Undecylenamido PEG-2 Sulfosuccinate, Disodium Wheat Germamido MEA-Sulfosuccinate, Disodium Wheat Germamido PEG-2 Sulfosuccinate, Di-TEA-Oleamido PEG-2 Sulfosuccinate, Ditridecyl Sodium Sulfosuccinate, Sodium Bisglycol Ricinosulfosuccinate, Sodium/MEA Laureth-2 Sulfosuccinate and Tetrasodium Dicarboxyethyl Stearyl Sulfosuccinamate. A further additional suitable sulfosuccinamate is disodium $C_{16-18}$-alkoxypropylene sulfosuccinamate.

In a preferred embodiment, the inventive agent comprises one or a plurality of sulfosuccinates, sulfosuccinamates and/or sulfosuccinamides, preferably sulfosuccinates and/or sulfosuccinamates, particularly sulfosuccinates, in quantities of typically 0.05 to 15 wt. %, advantageously 0.1 to 10 wt. %, particularly 0.3 to 6 wt. %, particularly preferably 0.5 to 3 wt. %, most preferably 0.7 to 2 wt. %, for example 0.75 or 1.5 wt. %.

The inventive agents can optionally comprise one or a plurality of non-ionic surfactants as additional components.

The added non-ionic surfactants are preferably alkoxylated, advantageously ethoxylated and/or propoxylated, particularly primary alcohols having preferably 8 to 18 carbon atoms and an average of 1 to 12 mol ethylene oxide (EO) and/or 1 to 10 mol propylene oxide (PO) per mol alcohol. $C_8$-$C_{16}$ alcohol alkoxylates, advantageously ethoxylated and/or propoxylated $C_{10}$-$C_{15}$ alcohol alkoxylates, particularly $C_{12}$-$C_{14}$ alcohol alkoxylates, with an ethoxylation degree between 2 and 10, preferably between 3 and 8, and/or a propoxylation degree between 1 and 6, preferably between 1.5 and 5, are particularly preferred. The alcohol group can preferably be linear or particularly preferably be methyl branched in the 2-position or comprise a mixture of linear and methyl-branched groups, as is typically present in oxo-alcohol groups. Particularly preferred are, however, alcohol ethoxylates with linear groups from alcohols of natural origin with 12 to 18 carbon atoms, e.g. from coco-, palm-, tallow- or oleyl alcohol, and an average of 2 to 8 EO per mol alcohol. Exemplary preferred ethoxylated alcohols include $C_{12-14}$ alcohols with 3 EO or 4 EO, $C_{9-11}$ alcohols with 7 EO, $C_{13-15}$ alcohols with 3 EO, 5 EO, 7 EO or 8 EO, $C_{12-18}$ alcohols with 3 EO, 5 EO or 7 EO and mixtures thereof, as well as mixtures of $C_{12-14}$ alcohols with 3 EO and $C_{12-18}$ alcohols with 5 EO. The cited degrees of ethoxylation and propoxylation constitute statistical average values that can be a whole or a fractional number for a specific product. Preferred alcohol ethoxylates and propoxylates have a narrowed homolog distribution (narrow range ethoxylates/propoxylates, NRE/NRP). In addition to these non-ionic surfactants, fatty alcohols with more than 12 EO can also be used. Examples of these are tallow fatty alcohol with 14 EO, 25 EO, 30 EO or 40 EO.

Alkoxylated amines, advantageously ethoxylated and/or propoxylated, particularly primary and secondary amines having preferably 1 to 18 carbon atoms per alkyl chain and an average of 1 to 12 mol ethylene oxide (EO) and/or 1 to 10 mol propylene oxide (PO) per mol amine, are also suitable.

Furthermore, as additional non-ionic surfactants, alkyl glycosides that satisfy the general Formula RO(G)x, can be added e.g. as compounds, particularly with anionic surfactants, where R means a primary linear or methyl-branched, particularly 2-methyl-branched, aliphatic group containing 8 to 22, preferably 12 to 18 carbon atoms and G stands for a glycose unit containing 5 or 6 carbon atoms, preferably for glucose. The degree of oligomerization x, which defines the distribution of monoglycosides and oligoglycosides, is any number between 1.0 and 10, preferably between 1.2 and 1.4.

Another class of preferred non-ionic surfactants which are used either as the sole non-ionic surfactant or in combination with other non-ionic surfactants, are alkoxylated, preferably ethoxylated or ethoxylated and propoxylated fatty acid alkyl esters preferably containing 1 to 4 carbon atoms in the alkyl chain, more particularly the fatty acid methyl esters which are described, for example, in Japanese patent application JP 58/217598 or which are preferably produced by the process described in International Patent application WO-A-90/13533.

Non-ionic surfactants of the amine oxide type, for example N-cocoalkyl-N,N-dimethylamine oxide and N-tallow alkyl-N,N-dihydroxyethylamine oxide, and the fatty acid alkanolamides may also be suitable.

The so-called Gemini surfactants can be considered as further surfactants. Generally speaking, such compounds are understood to mean compounds that have two hydrophilic groups and two hydrophobic groups per molecule. As a rule, these groups are separated from one another by a "spacer". The spacer is usually a hydrocarbon chain that is intended to be long enough such that the hydrophilic groups are a sufficient distance apart to be able to act independently of one another. These types of surfactants are generally characterized by an unusually low critical micelle concentration and the ability to strongly reduce the surface tension of water. In exceptional cases, however, not only dimeric but also trimeric surfactants are meant by the term Gemini surfactants.

Suitable Gemini surfactants are, for example, sulfated hydroxy mixed ethers according to German Patent application DE-A-43 21 022 or dimer alcohol bis- and trimer alcohol tris sulfates and ether sulfates according to the international patent application WO-A-96/23768. Blocked end group dimeric and trimeric mixed ethers according to German Patent application DE-A-195 13 391 are especially characterized by their bifunctionality and multifunctionality. Thus, the cited blocked end group surfactants possess good wetting properties and are therefore poor foamers and consequently they are particularly suited for use in automatic washing or cleaning processes.

However, Gemini polyhydroxyfatty acid amides or polyhydroxyfatty acid amides, such as those described in the International Patent applications WO-A-95/19953, WO-A-95/19954 and WO-A-95/19955 can also be used.

Other suitable surfactants are polyhydroxyfatty acid amides corresponding to the Formula (21),

in which $R^{64}CO$ stands for an aliphatic acyl group with to 6 to 22 carbon atoms, $R^{65}$ for hydrogen, an alkyl or hydroxyalkyl group with to 1 to 4 carbon atoms and [Z] for a linear or branched polyhydroxyalkyl group with 3 to 10 carbon atoms and 3 to 10 hydroxyl groups. The polyhydroxyfatty acid amides are known substances, which may normally be obtained by reductive amination of a reducing sugar with ammonia, an alkylamine or an alkanolamine and subsequent acylation with a fatty acid, a fatty acid alkyl ester or a fatty acid chloride.

The group of polyhydroxyfatty acid amides also includes compounds corresponding to the Formula (22),

in which $R^{66}$ is a linear or branched alkyl or alkenyl group containing 7 to 12 carbon atoms, $R^{67}$ is a linear, branched or cyclic alkyl group or an aryl radical containing 2 to 8 carbon atoms and $R^{68}$ is a linear, branched or cyclic alkyl group or an aryl group or an oxyalkyl group containing 1 to 8 carbon atoms, $C_{1-4}$ alkyl or phenyl radicals being preferred, and [Z] is a linear polyhydroxyalkyl radical, of which the alkyl chain is substituted by at least two hydroxyl groups, or alkoxylated, preferably ethoxylated or propoxylated derivatives of that group.

[Z] is preferably obtained by reductive amination of a reduced sugar, for example glucose, fructose, maltose, lactose, galactose, mannose or xylose. The N-alkoxy- or N-aryloxy-substituted compounds may then be converted, for example according to the teaching of the International application WO-A-95/07331, into the required polyhydroxyfatty acid amides by reaction with fatty acid methyl esters in the presence of an alkoxide as catalyst Preferred non-ionic surfactants are one or a plurality of linear or branched, saturated or unsaturated $C_{10-22}$ alcohols that are alkoxylated with ethylene oxide (EO) and/or propylene oxide (PO) with an alkoxylation degree of up to 30, preferably ethoxylated $C_{10-18}$ fatty alcohols with an ethoxylation degree of less than 30, preferably 1 to 20, particularly 1 to 12, particularly preferably 1 to 8, most preferably 2 to 5, for example $C_{12-14}$ fatty alcohol ethoxylates with 2, 3 or 4 EO or a mixture of the $C_{12-14}$ fatty alcohol ethoxylates with 3 and 4

EO in the weight ratio of 1 to 1 or isotridecyl alcohol ethoxylates with 5, 8 or 12 EO, such as for example described in DE 40 14 055 C2 (Grillo-Werke), to which reference is made and the contents of which are hereby incorporated into this application.

The non-ionic surfactants can normally be present in quantities of up to 50 wt. %, preferably from 0.1 to 40 wt. %, particularly preferably from 0.5 to 30 wt. %, especially from 2 to 25 wt. %, each based on the total agent.

In a preferred embodiment, the inventive agents are present in liquid form. In order to obtain a liquid consistence, it may be advisable to add both a liquid organic solvent as well as water. Thus, the inventive agents optionally comprise solvents.

Solvents that can be added to the inventive agents originate, for example, from the group of mono- or polyhydroxy alcohols, alkanolamines or glycol ethers, in so far that they are miscible with water in the defined concentrations. Preferably, the solvents are selected from ethanol, n- or i-propanol, butanols, glycol, propanediol or butanediol, glycerine, diglycol, propyldiglycol or butyldiglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl or propyl ether, butoxy propoxy propanol (BPP), dipropylene glycol methyl or ethyl ether, diisopropylene glycol methyl or ethyl ether, methoxy, ethoxy or butoxy triglycol, 1-butoxyethoxy-2-propanol, 3-methyl-3-methoxybutanol, propylene glycol t-butyl ether as well as mixtures of these solvents.

Some glycol ethers are available under the trade names Arcosolv® (Arco Chemical Co.) or Cellosolve®, Carbitol® or Propasol (Union Carbide Corp.); ButylCarbitol®, HexylCarbitol®, MethylCarbitol®, and Carbitol® itself, (2-(2-ethoxy)ethoxy)ethanol also belong to this group. The choice of the glycol ether can be easily made by the expert on the basis of volatility, water-solubility, content by percentage weight of the total dispersion and suchlike. Pyrrolidone solvents, such as N-alkyl pyrrolidones, for example N-methyl-2-pyrrolidone or N—$C_8$-$C_{12}$ alkyl pyrrolidone or 2-pyrrolidone can also be added. Further preferred as sole solvents or as a component of a mixture of solvents are glycerine derivatives, particularly glycerine carbonate.

Alcohols that can be added in the present invention as cosolvents include liquid polyethylene glycols with a low molecular weight, for example polyethylene glycol with a molecular weight of 200, 300, 400 or 600. Additional suitable cosolvents are other alcohols, for example (a) lower alcohols, such as ethanol, propanol, isopropanol and n-butanol, (b) ketones, such as acetone and methyl ethyl ketone, (c) $C_2$-$C_4$ polyols, such as a diol or a triol, for example ethylene glycol, propylene glycol, glycerine or mixtures thereof. From the class of diols, 1,2-octanediol is particularly preferred.

In a preferred embodiment, the agent comprises one or a plurality of solvents from the group that includes $C_1$-$C_4$ monoalcohols, $C_2$-$C_6$ glycols, $C_3$-$C_{12}$ glycol ethers and glycerine, particularly ethanol. The inventive $C_3$-$C_{12}$ glycol ethers comprise alkyl or alkenyl groups with less than 10 carbon atoms, preferably up to 8, particularly up to 6, particularly preferably 1 to 4 and most preferably 2 to 3 carbon atoms.

Preferred $C_1$-$C_4$ monoalcohols are ethanol, n-propanol, iso-propanol and tert.-butanol. Preferred $C_2$-$C_6$ glycols are ethylene glycol, 1,2-propylene glycol, 1,3-propylene glycol, 1,5-pentanediol, neopentyl glycol and 1,6-hexanediol, particularly ethylene glycol and 1,2-propylene glycol. Preferred $C_3$-$C_{12}$ glycol ethers are di-, tri-, tetra- and pentaethylene glycol, di-, tri- and tetrapropylene glycol, propylene glycol monotertiary butyl ether and propylene glycol monoethyl ether as well as the solvents designated according to INCI as butoxydiglycol, butoxyethanol, butoxyisopropanol, butoxypropanol, butyloctanol, ethoxydiglycol, ethoxyethanol, ethyl hexanediol, isobutoxyethanol, isopentyldiol, 3-methoxybutanol, methoxyethanol, methoxyisopropanol and methoxymethylbutanol.

In addition to the active detergent substances, builders and cobuilders are the most important ingredients of washing and cleaning agents. The inventive agents may contain any of the builders typically used in washing, rinsing and cleaning agents, i.e. in particular, zeolites, silicates, carbonates, organic co builders and also—where there are no ecological reasons preventing their use—phosphates.

Suitable crystalline, layered sodium silicates correspond to the general formula $NaMSi_xO_{2x+1}\cdot H_2O$, wherein M is sodium or hydrogen, x is a number from 1.9 to 4 and y is a number from 0 to 20, preferred values for x being 2, 3 or 4. These types of crystalline-layered silicates are described, for example, in the European Patent application EP-A-0 164 514. Preferred crystalline-layered silicates of the given formula, are those in which M stands for sodium and x assumes the values 2 or 3. Both β- and δ-sodium disilicate $Na_2Si_2O_5 \cdot yH_2O$ are particularly preferred, wherein β-sodium silicate can be obtained for example from the process described in the International Patent application WO-A-91/08171.

Other useful builders are amorphous sodium silicates with a modulus ($Na_2O$: $SiO_2$ ratio) of 1:2 to 1:3.3, preferably 1:2 to 1:2.8 and more preferably 1:2 to 1:2.6, which dissolve with a delay and exhibit multiple wash cycle properties. The delay in dissolution compared with conventional amorphous sodium silicates can have been obtained in various ways, for example by surface treatment, compounding, compressing/compacting or by over-drying. In the context of this invention, the term "amorphous" also means "X-ray amorphous". In other words, the silicates do not produce any of the sharp X-ray reflexions typical of crystalline substances in X-ray diffraction experiments, but at best one or more maxima of the scattered X-radiation, which have a width of several degrees of the diffraction angle. However, particularly good builder properties may even be achieved where the silicate particles produce indistinct or even sharp diffraction maxima in electron diffraction experiments. This can be interpreted to mean that the products have microcrystalline regions between 10 and a few hundred nm in size, values of up to at most 50 nm and especially up to at most 20 nm being preferred. This type of X-ray amorphous silicates, which similarly possess a delayed dissolution in comparison with the customary water glasses, are described, for example in the German Patent application DE-A-44 00 024. Compacted/densified amorphous silicates, compounded amorphous silicates and over dried X-ray-amorphous silicates are particularly preferred.

Of the optionally suitable fine crystalline, synthetic zeolites containing bound water, zeolite A and/or P are preferred. A particularly preferred zeolite P is zeolite MAP (e.g. commercial product Doucil A24 of Crosfield). However, the zeolites X as well as mixtures of A, X and/or P are also suitable. Commercially available and preferred in the context of the present invention is, for example, also a co-crystallizate of zeolite X and zeolite A (ca. 80 wt. % zeolite X), which is marketed under the name of VEGOBOND AX® by CONDEA Augusta S.p.A. Suitable zeolites have an average particle size of less than 10 nm (volume distribution; measured with a Coulter Counter) and preferably comprise 18 to 22 wt. %, particularly 20 to 22 wt. % of bound water.

Naturally, the generally known phosphates can also be added as builders, in so far that their use should not be avoided on ecological grounds. The sodium salts of the orthophosphates, the pyrophosphates and especially the tripolyphosphates are particularly suitable.

Useful organic builders are, for example, the polycarboxylic acids usable in the form of their sodium salts, polycarboxylic acids in this context being understood to be carboxylic acids that carry more than one acid function. These include, for example, citric acid, adipic acid, succinic acid, glutaric acid, malic acid, tartaric acid, maleic acid, fumaric acid, sugar acids, aminocarboxylic acids, nitrilotriacetic acid (NTA), providing its use is not ecologically unsafe, and mixtures thereof. Preferred salts are the salts of polycarboxylic acids such as citric acid, adipic acid, succinic acid, glutaric acid, tartaric acid, sugar acids and mixtures thereof. Acids per se can also be used. Besides their building effect, the acids also typically have the property of an acidifying component and, hence also serve to establish a relatively low and mild pH in washing and cleaning agents according to the invention. Citric acid, succinic acid, glutaric acid, adipic acid, gluconic acid and any mixtures thereof are particularly mentioned in this regard.

Polymeric polycarboxylates are also suitable as builders. They are for example the alkali metal salts of polyacrylic or polymethacrylic acid, for example those with a relative molecular weight of 500 to 70,000 g/mol.

The molecular weights mentioned in the context of the present invention for polymeric polycarboxylates are weight-average molecular weights Mw of the particular acid form which, fundamentally, were determined by gel permeation chromatography (GPC), using a UV detector. The measurement was carried out against an external polyacrylic acid standard, which provides realistic molecular weight values by virtue of its structural similarity to the polymers investigated. These values differ distinctly from the molecular weights measured against polystyrene sulfonic acids as standard. The molecular weights measured against polystyrene sulfonic acids are generally higher than the molecular weights mentioned in the present invention.

Particularly suitable polymers are polyacrylates, which preferably have a molecular weight of 2,000 to 20,000 g/mol. By virtue of their superior solubility, preferred representatives of this group are again the short-chain polyacrylates, which have molecular weights of 2,000 to 10,000 g/mol and, more particularly, 3,000 to 5,000 g/mol.

In addition, copolymeric polycarboxylates are suitable, particularly those of acrylic acid with methacrylic acid and of acrylic acid or methacrylic acid with maleic acid. Copolymers of acrylic acid with maleic acid, which comprise 50 to 90 wt. % acrylic acid and 50 to 10 wt. % maleic acid, have proven to be particularly suitable. Their relative molecular weight, based on free acids, generally ranges from 2000 to 70,000 g/mol, preferably 20,000 to 50,000 g/mol and especially 30,000 to 40,000 g/mol.

The (co)polymeric polycarboxylates can be added either as powders or as aqueous solutions. The (co)polymeric polycarboxylate content of the inventive agent is preferably from 0.5 to 20% by weight, in particular from 3 to 10% by weight.

In order to improve the water solubility, the polymers can also comprise allylsulfonic acids as monomers, such as for example, allyloxybenzene sulfonic acid and methallylsulfonic acid in EP-B 0 727 448.

Particular preference is also given to biodegradable polymers comprising more than two different monomer units, examples being those comprising, as monomers, salts of acrylic acid and of maleic acid, and also vinyl alcohol or vinyl alcohol derivatives, as in DE-A 43 00 772, or those comprising, as monomers, salts of acrylic acid and of 2-alkylallylsulfonic acid, and also sugar derivatives as in DE-C-42 21 381.

Further preferred copolymers are those that are described in the German Patent applications DE 43 03 320 and DE 44 17 734 and preferably have acrolein and acrylic acid/acrylic acid salts or acrolein and vinyl acetate as monomers.

Similarly, other preferred builders are polymeric aminodicarboxylic acids, salts or precursors thereof. Those polyaspartic acids or their salts and derivatives disclosed in the German Patent application DE-A 195 40 086 as having a bleach-stabilizing action in addition to cobuilder properties are particularly preferred.

Other suitable builders are polyacetals, which may be obtained by reaction of dialdehydes with polyol carboxylic acids containing 5 to 7 carbon atoms and at least three hydroxyl groups, for example like those described in the European Patent application EP-A 0 280 223. Preferred polyacetals are obtained from dialdehydes, such as glyoxal, glutaraldehyde, terephthalaldehyde and mixtures thereof and from polyol carboxylic acids, such as gluconic acid and/or glucoheptonic acid.

Further suitable organic builders are dextrins, for example oligomers or polymers of carbohydrates that can be obtained by the partial hydrolysis of starches. The hydrolysis can be carried out using typical processes, for example acidic or enzymatic catalysed processes. The hydrolysis products preferably have average molecular weights in the range 400 to 500,000 g/mol. A polysaccharide with a dextrose equivalent (DE) of 0.5 to 40 and, more particularly, 2 to 30 is preferred, the DE being an accepted measure of the reducing effect of a polysaccharide by comparison with dextrose, which has a DE of 100. Both maltodextrins with a DE between 3 and 20 and dry glucose syrups with a DE between 20 and 37 and also so-called yellow dextrins and white dextrins with relatively high molecular weights of 2000 to 30,000 g/mol may be used. A preferred dextrin is described in the British Patent application 94 19 091.

The oxidized derivatives of such dextrins are their products of reaction with oxidizing agents that are capable of oxidizing at least one alcohol function of the saccharide ring to the carboxylic acid function. Such oxidized dextrins and processes for their manufacture are known particularly from the European Patent applications EP-A 0 232 202, EP-A 0 427 349, EP-A 0 472 042 and EP-A 0 542 496 as well as from the International Patent applications WO 92/18542, WO 93/08251, WO 93/16110, WO 94/28030, WO 95/07303, WO 95/12619 and WO 95/20608. An oxidized oligosaccharide according to the German Patent application DE-A 196 00 018 is also suitable. A product oxidized at C6 of the saccharide ring can be particularly advantageous.

Oxydisuccinates and other derivatives of disuccinates, preferably ethylene diamine disuccinate are also further suitable cobuilders. Here, ethylene diamine-N,N'-disuccinate (EDDS), the synthesis of which is described for example in the text of U.S. Pat. No. 3,158,615, is preferably used in the form of its sodium or magnesium salt. Moreover, in this context, glycerine disuccinates and glycerine trisuccinates are preferred, such as those described in the U.S. Pat. Nos. 4,524,009 and 4,639,325, in the European Patent application EP-A 0 150 930 and in the Japanese Patent application JP-A 93/339,896. Suitable addition quantities in zeolite-containing and/or silicate-containing formulations range from 3 to 15% by weight.

Other useful organic co-builders are, for example, acetylated hydroxycarboxylic acids and salts thereof which may optionally be present in lactone form and which contain at least 4 carbon atoms, at least one hydroxyl group and at most two acid groups. Such cobuilders are described, for example, in the International Patent application WO 95/20029.

Phosphonates represent a further class of substances with cobuilder properties. In particular, they are hydroxyalkane phosphonates or aminoalkane phosphonates. Among the hydroalkane phosphonates, 1-hydroxyethane-1,1-diphosphonate (HEDP) is a particularly important cobuilder. It is normally added as its sodium salt, the disodium salt reacting neutral and the tetrasodium salt reacting alkaline (pH=9). Ethylene diamine tetramethylene phosphonate (EDTMP), Diethylene triamine pentamethylene phosphonate (DTPMP) and their higher homologs are preferably chosen as aminoalkane phosphonates. They are preferably added in the form of their neutral-reacting sodium salts, e.g. as the hexasodium salt of EDTMP or as the hepta and octasodium salt of DTPMP. Of the phosphonates, HEDP is preferably used as a builder. The aminoalkane phosphonates additionally possess a pronounced ability to complex heavy metals. Accordingly, it can be preferred, particularly where the inventive agents also contain bleach, to use aminoalkane phosphonates, particularly DTPMP, or mixtures of the phosphonates mentioned.

In addition, any compounds capable of forming complexes with alkaline earth metal ions may be used as co-builders.

In a preferred embodiment, the inventive agent optionally comprises, in addition, one or a plurality of chelating agents.

The INCI termed chelating agents are also known as sequestrants and are ingredients that are capable of complexing and inactivating metal ions so as to prevent their detrimental action on the stability or on the appearance of the agent, e.g. turbidity. It is important to complex the calcium and magnesium ions in hard water, as they are incompatible with numerous ingredients. Complexing heavy metal ions like iron or copper slows down the oxidative decomposition of the finished agent.

Further suitable chelating agents as named in INCI are for example the following that are described in more detail in the *International Cosmetic Ingredient Dictionary and Handbook*: aminotrimethylene phosphonic acid, beta-alanine diacetic acid, calcium disodium EDTA, citric acid, cyclodextrin, cyclohexanediamine tetraacetic acid, diammonium citrate, diammonium EDTA, diethylenetriamine pentamethylene phosphonic acid, dipotassium EDTA, disodium azacycloheptane diphosphonate, disodium EDTA, disodium pyrophosphate, EDTA, etidronic acid, galactaric acid, gluconic acid, glucuronic acid, HEDTA, hydroxypropyl cyclodextrin, methyl cyclodextrin, pentapotassium triphosphate, pentasodium aminotrimethylene phosphonate, pentasodium ethylenediamine tetramethylene phosphonate, pentasodium pentetate, pentasodium triphosphate, pentetic acid, phytic acid, potassium citrate, potassium EDTMP, potassium gluconate, potassium polyphosphate, potassium trisphosphonomethylamine oxide, ribonic acid, sodium chitosan methylene phosphonate, sodium citrate, sodium diethylenetriamine pentamethylene phosphonate, sodium dihydroxyethylglycinate, sodium EDTMP, sodium gluceptate, sodium gluconate, sodium glycereth-1 polyphosphate, sodium hexametaphosphate, sodium metaphosphate, sodium metasilicate, sodium phytate, sodium polydimethylglycinophenolsulfonate, sodium trimetaphosphate, TEA-EDTA, TEA-polyphosphate, tetrahydroxyethyl ethylenediamine, tetrahydroxypropyl ethylenediamine, tetrapotassium etidronate, tetrapotassium pyrophosphate, tetrasodium EDTA, tetrasodium etidronate, tetrasodium pyrophosphate, tripotassium EDTA, trisodium dicarboxymethyl alaninate, trisodium EDTA, trisodium HEDTA, trisodium NTA and trisodium phosphate.

Preferred chelating agents are tertiary amines, particularly tertiary alkanolamines (amino alcohols). The alkanolamines possess both amino and hydroxyl and/or ether groups as functional groups. Particularly preferred tertiary alkanolamines are triethanolamine and tetra-2-hydroxypropyl ethylene diamine (N,N,N',N'-tetrakis-(2-hydroxypropyl)ethylene diamine). Particularly preferred combinations of tertiary amines with zinc ricinoleate and one or a plurality of ethoxylated fatty alcohols as the non-ionic solubilizer as well as optional solvents are described in DE 40 14 055 C2 (Grillo-Werke) to which reference is made in this context and the contents of which are hereby incorporated into this application.

A particularly preferred chelating agent is the etidronic acid (1-hydroxyethylidene-1,1-diphosphonic acid, 1-hydroxyethane-1,1-diphosphonic acid, HEDP, acetophosphonic acid, INCI Etidronic Acid) including its salts. In a preferred embodiment, the inventive agent accordingly comprises etidronic acid and/or one or more of its salts as the chelating agent.

In a preferred embodiment, the inventive agent comprises a combination of chelating agents from one or a plurality of tertiary amines and one or a plurality of additional chelating agents, preferably one or a plurality of chelating acids or their salts, particularly from triethanolamine and/or tetra-2-hydroxypropyl ethylene diamine and etidronic acid and/or one or a plurality of its salts.

The inventive agent comprises chelating agents in quantities of typically 0 to 20 wt. %, advantageously 0.1 to 15 wt. %, particularly 0.5 to 10 wt. %, particularly preferably 1 to 8 wt. %, most preferably 1.5 to 6 wt. %, for example 1.5, 2.1, 3 or 4.2 wt. %.

In a further embodiment, the inventive agent optionally comprises one or a plurality of viscosity regulators that preferably function as thickeners.

The viscosity of the agent can be measured using standard methods (for example using a Brookfield-Viscosimeter RVD-VII at 20 rpm and 20° C., spindle 3) and lies preferably in the range from 10 to 5000 mPas. Preferred agents in liquid to gel form have viscosities from 20 to 4000 mpas, particularly preferably from 40 to 2000 mPas.

Suitable thickeners are inorganic or polymeric organic compounds. Mixtures of a plurality of thickeners can also be used.

The inorganic thickeners include, for example, polysilicic acids, mineral clays like montmorillonite, zeolites, silicic acids, aluminum silicates, layered silicates and bentonites.

The organic thickeners come from the groups of natural polymers, derivatives of natural polymers and synthetic polymers.

Exemplary, naturally occurring polymers that can be used as thickeners are xanthane, agar agar, carrageen, tragacanth, gum Arabic, alginates, pectins, polyoses, guar meal, galan gum, locust tree bean flour, starches, dextrins, gelatines and casein.

Modified natural products occur mainly from the group of modified starches and celluloses, examples being carboxymethyl cellulose and other cellulose ethers, hydroxyethyl and hydroxypropyl cellulose, highly etherified methyl hydroxyethyl cellulose as well as bean flour ether.

A major group of thickeners that are widely used in the most varied applications are the synthetic polymers such as polyacrylic and polymethacrylic compounds that can be crosslinked or non-crosslinked and optionally cationically modified, vinyl polymers, polycarboxylic acids, polyethers, activated polyamide derivatives, castor oil derivatives, polyimines, polyamides and polyurethanes. Exemplary polymers are acrylic resins, ethyl acrylate acrylamide copolymers, acrylate ester methacrylate ester copolymers, ethyl acrylate acrylic acid methacrylic acid copolymers, N-methylol methacrylamide, maleic anhydride methyl vinyl ether copolymers, polyether polyol copolymers as well as butadiene styrene copolymers.

Additional suitable thickeners are derivatives of organic acids as well as their alkoxide adducts, for example aryl polyglycol ethers, carboxylated nonylphenol ethoxylate derivatives, sodium alginate, diglycerin monoisostearate, non-ionic ethylene oxide adducts, coco fatty acid diethanolamide, isododecenyl succinic anhydride as well as galactomannan.

Thickeners from the cited classes of substances are commercially available and offered, for example, under the trade names Acusol®-820 (methacrylic acid(stearylalkohol-20-EO)ester-acrylic acid copolymer, 30% in water, Rohm & Haas), Dapral®-GT-282-S (alkylpolyglycol ether, Akzo), Deuterol®-Polymer-11 (dicarboxylic acid copolymer, Schöner GmbH), Deuteron®-XG (anionic heteropolysaccharide based on b-D-glucose, D-manose, D-glucuronic acid, Schöner GmbH), Deuteron®-XN (non-iogenic polysaccharide, Schöner GmbH), Dicrylan®-Verdicker-O (ethylene oxide adduct, 50% in water/isopropanol, Pfersse Chemie), EMA®-81 and EMA®-91 (ethylene-maleic anhydride copolymer, Monsanto), Verdicker-QR-1001 (polyurethane emulsion, 19-21% in water/diglycol ether, Rohm & Haas), Mirox®-AM (anionic acrylic acid acrylate copolymer dispersion, 25% in water, Stockhausen), SER-AD-FX-1100 (hydrophobic urethane polymer, Servo Delden), Shellflo®-S (high molecular weight polysaccharide, stabilized with formaldehyde, Shell), Shellflo®-XA (Xanthane biopolymer, stabilized with formaldehyde, Shell), Kelzan, Keltrol T (Kelco).

In a further embodiment, the inventive agent optionally comprises one or a plurality of enzymes.

Suitable enzymes are, in particular, those from the classes of hydrolases, such as proteases, esterases, lipases or lipolytic enzymes, amylases, cellulases or other glycosyl hydrolases and mixtures thereof. In the wash, all these hydrolases contribute to removing stains such as protein, fat or starchy stains and against graying. Moreover, cellulases and other glycosyl hydrolases can contribute to increased softness of the textile and to color retention by removing pilling and micro fibrils. Oxireductases can also be added for bleaching or for reducing color transfer. Enzymatic active materials obtained from bacterial sources or fungi such as *bacillus subtilis, bacillus licheniformis, streptomyceus griseus* and *humicola insolens* are particularly well suited. Proteases of the subtilisin type and particularly proteases that are obtained from *bacillus lentus*, are preferably used. Here, mixtures of enzymes are of particular interest, for example proteases and amylases or proteases and lipases or lipolytic enzymes or proteases and cellulases or cellulases and lipase or lipolytic enzymes or proteases, amylases and lipases or lipolytic enzymes or proteases, lipases or lipolytic enzymes and cellulases, in particular, however proteases and/or lipase-containing mixtures or mixtures with lipolytic enzymes. Examples of such lipolytic enzymes are the known cutinases. Peroxidases or oxidases have also proved to be suitable in certain cases. The suitable amylases particularly include α-amylases, iso-amylases, pullulanases and pectinases. Cellobiohydrolases, endoglucanases and β-glucosidases or mixtures thereof, which are also known as cellobiases, are preferred cellulases. As the different cellulase types differ in their CMCase and avicelase activities, the required activities can be adjusted by controlled mixtures of the cellulases.

The enzymes can be embedded, adsorbed or coated on carriers as tablets so as to protect them against premature decomposition. The content of the enzymes, enzyme mixtures or enzyme granules may be, for example, about 0.1 to 5% by weight and is preferably 0.12 to about 2% by weight.

The agents can optionally comprise additional bleaching agents. Among the compounds, which serve as bleaches and liberate $H_2O_2$ in water, sodium percarbonate, sodium perborate tetrahydrate and sodium perborate monohydrate are of particular importance. Examples of further bleaching agents, which may be used, are peroxypyrophosphates, citrate perhydrates and $H_2O_2$-liberating peracidic salts or peracids, such as persulfates or persulfuric acid. The urea peroxyhydrate, percarbamide, $H_2N-CO-NH_2.H_2O_2$ is also suitable. Particularly when agents are used to clean hard surfaces, for example for automatic dishwashers, they can, if desired, also comprise bleaching agents from the group of organic bleaching agents, although in principal they can also be used for washing textiles. Typical organic bleaching agents are the diacyl peroxides, such as e.g. dibenzoyl peroxide. Further typical organic bleaching agents are the peroxy acids, wherein the alkylperoxy acids and the arylperoxy acids may be named as examples. Preferred representatives that can be added are peroxybenzoic acid and ring-substituted derivatives thereof, such as alkyl peroxybenzoic acids, but also peroxy-α-naphthoic acid and magnesium monoperphthalate, the aliphatic or substituted aliphatic peroxy acids, such as peroxylauric acid, peroxystearic acid, ε-phthalimidoperoxycaproic acid [phthaloiminoperoxyhexanoic acid (PAP)], o-carboxybenzamidoperoxycaproic acid, N-nonenylamido peradipic acid and N-nonenylamido persuccinates and (c) aliphatic and araliphatic peroxydicarboxylic acids, such as 1,12-diperoxycarboxylic acid, 1,9-diperoxyazelaic acid, diperoxysebacic acid, diperoxybrassylic acid, diperoxyphthalic acids, 2-decyldiperoxybutane-1,4-dioic acid, N,N-terephthaloyl-di(6-aminopercaproic acid).

The bleaching agents can be coated to protect them against premature decomposition.

Dyes can be added to the inventive agents, the quantity of one or several dyes being as low as possible such that no visible residues remain after having used the agent. Preferably, however, the inventive agent is free of dyes.

In addition, the agents can optionally comprise UV-absorbers that for example absorb onto the treated substrate and improve the fastness of the substrate and/or the fastness of various formulation components. UV-absorbers are understood to mean organic compounds that are able to absorb ultra violet radiation and emit the resulting energy in the form of longer wavelength radiation, for example as heat. Compounds, which possess these desired properties, are for example, the efficient radiationless deactivating compounds and derivatives of benzophenone having substituents in position(s) 2 and/or 4. Also suitable are substituted benzotriazoles, such as for example the water-soluble sodium salt of 3-(2H-benzotriazole-2-yl)-4-hydroxy-5-(methylpropyl) benzenesulfonic acid (Cibafast® H), acrylates, which are phenyl-substituted in position 3 (cinnamic acid derivatives) optionally with cyano groups in position 2, salicylates, organic Ni complexes, as well as natural substances such as umbelliferone and the endogenous urocanic acid. The biphenyl derivatives and above all the stilbene derivatives, such as for example, those described in EP 0728749 A and commercially available as Tinosorb® FD or Tinosorb® FR from Ciba, are of particular importance. As UV-B absorbers can be cited: 3-benzylidenecamphor or 3-benzylidenenorcamphor and its derivatives, for example 3-(methylbenzylidene) camphor, as described in EP 0693471 B1; 4-aminobenzoic acid derivatives, preferably the 2-ethylhexyl ester of 4-(dimethylamino)benzoic acid, the 2-octyl ester of 4-(dimethylamino) benzoic acid, and the amyl ester of 4-(dimethylamino)benzoic acid; esters of cinnamic acid, preferably the 2-ethylhexyl ester of 4-methoxycinnamic acid, the propyl ester of 4-methoxycinnamic acid, the isoamyl ester of 4-methoxycinnamic acid, the 2-ethylhexyl ester of 2-cyano-3,3-phenylcinnamic acid, (octocrylene); esters of salicylic acid, preferably 2-ethylhexyl salicylate, 4-isopropylbenzyl salicylate, homomenthyl salicylate; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably 4-methoxybenzmalonic acid, di-2-ethylhexylester; triazine derivatives, such as, for example 2,4,6-trianilino-(p-carbo-2'-ethyl-1'-hexyloxy)-1,3,5-triazine and octyl triazone, as described in EP 0818450 A1 or dioctyl butamidotriazone (Uvasorb® HEB); propane-1,3-diones, such as for example 1-(4-tert.butylphenyl)-3-(4'-methoxyphenyl)propane-1,3-dione; ketotricyclo(5.2.1.0)decane derivatives, such as are described in EP 0694521 B1. Further suitable are 2-phenylbenzimidazole-5-sulfonic acid and its alkali-, alkaline earth-, ammonium-, alkylammonium-, alkanolammonium- and glucammonium salts; sulfonic acid derivatives of benzophenones, preferably 2-hydroxy-4-methoxybenzophenone-5-sulfonic acid and its salts; sulfonic acid derivatives of 3-benzylidene camphor, such as for example 4-(2-oxo-3-bornylidenemethyl)benzene sulfonic acid and 2-methyl-5-(2-oxo-3-bornylidene) sulfonic acid and its salts.

Typical UV-A filters particularly include derivatives of benzoylmethane, such as, for example 1-(4'-tert.-butylphenyl)-3-(4'-methoxyphenyl)propane-1,3-dione, 4-tert.-butyl-4'-methoxydibenzoylmethane (Parsol 1789), 1-phenyl-3-(4'-isopropylphenyl)-propane-1,3-dione as well as enamine compounds, as described in the DE 19712033 A1 (BASF). Naturally, the UV-A and UV-B filters can also be added as mixtures. Beside the cited soluble materials, insoluble, light-protecting pigments, namely finely dispersed, preferably, nano metal oxides or salts can also be considered for this task. Exemplary suitable metal oxides are particularly zinc oxide and titanium oxide and also oxides of iron, zirconium, silicon, manganese, aluminum and cerium as well as their mixtures. Silicates (talc), barium sulfate or zinc stearate can be added as salts. The oxides and salts are already used in the form of pigments for skin care and skin protecting emulsions and decorative cosmetics. Here, the particles should have a mean diameter of less than 100 nm, preferably between 5 and 50 nm and especially between 15 and 30 nm. They can be spherical, however elliptical or other shaped particles can also be used. The pigments can also be surface treated, i.e. hydrophilized or hydrophobized. Typical examples are coated titanium dioxides, such as, for example Titandioxid T 805 (Degussa) or Eusolex® T2000 (Merck). Hydrophobic coating agents preferably include trialkoxy octylsilanes or Simethicones. Micronized zinc oxide is preferably used. Further suitable UV light protection filters may be found in the review by P. Finkel in SöFW Journal, Volume 122 (1996), p. 543.

The UV absorbers are normally used in amounts of 0.01 wt. % to 5 wt. %, preferably from 0.03 wt. % to 1 wt. %.

In addition, the agents, in so far as they are textile treatment products, can optionally comprise ironing auxiliaries to improve the water-absorption capacity, the wettability of the treated textiles and to facilitate ironing of the treated textiles. For example, silicone derivatives can be added into the formulations. They additionally improve the final rinse behavior of the wash-active formulation by their foam-inhibiting properties. Exemplary preferred silicone derivatives are polydialkylsiloxanes or alkylarylsiloxanes, in which the alkyl groups possess one to five carbon atoms and are totally or partially fluorinated. Preferred silicones are polydimethylsiloxanes that can be optionally derivatized and then be aminofunctional or quaternized or possess Si—OH, Si—H and/or SiCl bonds. The viscosities of the preferred silicones at 25° C. are in the range between 100 and 100,000 mPas, wherein the silicones can be added in amounts between 0.2 and 5 wt. % based on the total agent.

In addition, the agents can optionally comprise anti-crease agents or crease-reduction agents. These include, for example, synthetic products based on fatty acids, fatty acid esters, fatty acid amides, fatty acid alkylol esters, fatty acid alkylol amides or fatty alcohols that have been mainly treated with ethylene oxide, or products based on lecithin or modified phosphoric acid esters.

The inventive agents can be used for a plurality of applications. A preferred embodiment is the use of an inventive agent as a cosmetic formulation. This can be any cosmetic formulation that can serve as a care, cleaning or beauty product for the body, from deodorants through hair care to dental care, to name only three particular examples.

A further preferred embodiment relates to the use of the inventive agent as a textile treatment product. In particular, they are detergents or textile treatment products or rinses or softeners.

In a further preferred embodiment, an inventive agent is used for cleaning and/or the care of hard surfaces, for example for cleaning crockery, porcelain or ceramics, floors or glass etc.

A further preferred embodiment is constituted by the use of an inventive agent for conditioning keratin-containing fibers, particularly using a spray dispenser.

Another preferred embodiment consists in a product comprising an inventive agent and a spray dispenser.

The preferred spray dispenser is a manually operated spray dispenser, selected in particular from the group that includes aerosol spray dispensers, self generated pressure spray dispensers, pump spray dispensers and trigger spray dispensers, particularly pump spray dispensers and trigger spray dispensers, advantageously with a container of transparent polyethylene or polyethylene terephthalate.

These spray dispensers and the like or related devices for the application are commercially available and all commercially available spray dispensers or related devices for the application can be considered for the inventive application.

Accordingly, a further subject of the invention is a process for treating hard or soft substrates or substrate surfaces, in which an effective amount of an inventive agent is applied to the substrate to be treated, preferably by means of a product that has just been described, preferably by spraying, with the proviso that the agent is in liquid form, in particular emulsified. An effective amount is understood to mean an amount that permits a desired treatment result to be obtained. This amount depends on many factors, such as e.g. substrate type and state, the required or realizable result.

In a preferred embodiment of the just cited process, the inventive agent is sprayed onto the substrate to be treated, particularly using an inventive product, particularly from a distance of 10 to 100 cm, advantageously 20 to 50 cm, particularly preferably 25 to 40 cm, most preferably from about 30 cm.

The particular advantage of the abovementioned subject that relates to the use of a spray dispenser, resides in the fact that the sprayed agent adheres particularly well to the substrate and therefore enables an efficient release of the active principles.

A further subject of the invention is a conditioning substrate that is coated and/or saturated with an inventive agent. The development form of the impregnation or treatment agent or saturation agent is to be taken from the previous description.

Conditioning substrates are mainly used in textile treatment and particularly in textile drying processes. The substrate material preferably consists of porous, flat cloths. They can consist of a fibrous or cellular, flexible material that exhibits sufficient thermal stability in the drier and can retain the sufficient amount of an impregnation or coating material to effectively condition materials, without an appreciable leakage or exudation of the agent occurring during storage. These cloths include cloths of woven and non-woven synthetic and natural fibers, felt, paper or foam, such as hydrophilic polyurethane foam.

Preferably, typical cloths of non-woven material (fleece, particularly viscose fleece) are used. Fleeces are generally defined as adhesively bonded fibrous products that possess a matted or layered fiber structure, or those that include fiber mats, in which the fibers are distributed randomly or statistically. The fibers can be of natural origin, such as wool, silk, jute, cotton, linen, sisal or ramie; or synthetic, such as rayon, cellulose esters, polyvinyl derivatives, polyolefins, polyamides or polyester. In general, each fiber diameter or yarn count is suitable for the present invention. The non-woven materials used here, due to the random or statistical distribution of the fibers that lend the excellent strength in all directions, do not tend to tear or disintegrate when they are used, for example, in a typical household washing drier. Examples of non-woven materials that are suitable substrates in the present invention, are known, for example, from WO 93/23603. Preferred porous and flat conditioning cloths consist of one or various fiber materials, particularly from cotton, refined cotton, polyamide, polyester or mixtures of these. Preferably, the conditioning substrates in the form of cloth exhibit a surface from 0.2 to 0.005 $m^2$, preferably from 0.15 to 0.01 $m^2$, particularly from 0.1 to 0.03 $m^2$ and particularly preferably from 0.09 to 0.06 $m^2$. The grammage of the material is normally between 20 and 1,000 $g/m^2$, advantageously from 30 to 500 $g/m^2$ and particularly from 50 to 150 $g/m^2$. Conditioning substrates can be obtained by saturating or impregnating or even by melting the inventive agent or conditioning agent on the substrate.

Accordingly, a further subject of this invention is a process for conditioning textiles in which one or a plurality of conditioning substrates are used in a textile drying process according to the just mentioned practices.

A further subject of the invention is the use of a compound that preferably carries at least one cationic charge and which is absorbed on hard and/or soft surfaces of substrates, to fix an oligomer, polymer or copolymer that comprises the following structural element shown in Formula (1) at least once, on hard and/or soft substrate surfaces.

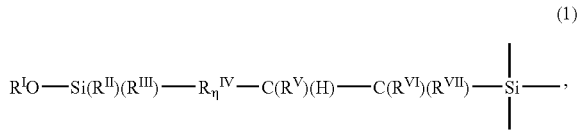

(1)

EXAMPLES

In order to assess the inventive agents, several comparative experiments in the form of washing tests and rinsing tests were carried out. Each of the detergents or softeners were compared and in absolute terms contained approximately the same concentration of fragrance, here phenylethyl alcohol. The sole difference was that in the inventive cases, the fragrance was incorporated in the form of a silicone derivative, whereas the fragrance was directly incorporated for the comparative tests.

Eight test evaluators participated for each of the comparative tests and assessed the intensity of the fragrance, each based on the odor of the product as such, as well as the odor of the washing in the wet and in the dry state. By wet state is meant that after spin-drying, the wet washing was taken out of the drum and its odor was assessed. The washing was then dried on the washing line. The scent of the washing was assessed after one day, 3, 7 and 14 days, the dry washing being carefully stored and separated from each other in open plastic bags. Then the samples were assessed in a pair test, the winner obtaining 1 point and the loser 0 points. This means that the highest point count was also the best performer, but also that the samples with a 0 point performance are not odorless, but were only assessed as being poorer in the comparison. For each pair, each pair comparison was repeated 4 times by each evaluator.

In the inventive examples, the silicone derivatives A and B were used. They are the following compounds:

Silicone derivative A:

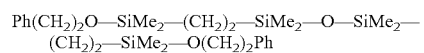

The phenyethyl alcohol group content is ca. 45 wt. % based on the silicone derivative A.

Silicone derivative B:

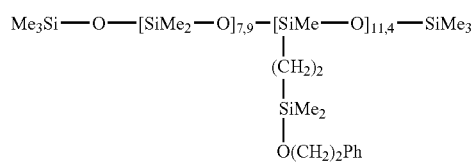

The phenyethyl alcohol group content is ca. 37 wt. % based on the silicone derivative B.

Example 1

Basic material: 99 wt. % of a commercial perfume-free detergent and 1 part by weight Rewoquat® WE 18; (ditallow carboxyethyl)-hydroxyethyl methyl ammonium methosulfate; Producer: (Degussa) and the quantities of the perfume oil or the silicone derivative given in Table 1; total weight of detergent, including Rewoquat® WE 18: 146 g; wash temperature: 60° C.; standard washing program for colored wash; washing machine type Miele Novotronic W135

TABLE 1

| | | Preference for the intensity of the odor | | | | |
|---|---|---|---|---|---|---|
| Perfume oil | Product | washing wet | washing dry 1 day | washing dry 3 days | washing dry 7 days | washing dry 14 days |
| 0.4 parts by wt. Phenylethyl alcohol | 8 | 1 | 0 | 1 | 0 | 0 |

TABLE 1-continued

| Perfume oil | Product | washing wet | washing dry 1 day | washing dry 3 days | washing dry 7 days | washing dry 14 days |
|---|---|---|---|---|---|---|
| 0.89 parts by wt. Silicone derivative A | 0 | 4 | 7 | 6 | 8 | 8 |

Preference for the intensity of the odor

For the wet washing, 3 evaluators could not distinguish any difference in the intensity of the odor, after one day and 3 days for the dry washing, one evaluator could not distinguish any difference in the intensity of each odor.

Example 2

Basic material: 99 wt. % of a commercial perfume-free detergent and 1 part by weight Rewoquat® WE 18; (ditallow carboxyethyl)-hydroxyethyl methyl ammonium methosulfate; Producer: (Degussa) and the quantities of the perfume oil or the silicone derivative given in Table 2; total weight of detergent, including Rewoquat® WE 18: 146 g; wash temperature: 60° C.; standard washing program for colored wash; washing machine type Miele Novotronic W135.

TABLE 2

| Perfume oil | Product | washing wet | washing dry 1 day | washing dry 3 days | washing dry 7 days | washing dry 14 days |
|---|---|---|---|---|---|---|
| 0.4 parts by wt. Phenylethyl alcohol | 8 | 7 | 0 | 0 | 0 | 0 |
| 1.08 parts by wt. Silicone derivative B | 0 | 0 | 5 | 7 | 6 | 8 |

Preference for the intensity of the odor

For the wet washing, 1 evaluator could not distinguish any difference in the intensity of the odor, after one day for dry washing, 3 evaluators could not distinguish any difference, after 3 days for the dry washing, one evaluator could not distinguish any difference, after 7 days for dry washing 2 evaluators could not distinguish any difference.

Example 3

Basic material: 99 wt. % of a commercial perfume-free softener rinse comprising ca. 17 parts by weight Rewoquat® WE 18; (ditallow carboxyethyl)-hydroxyethyl methyl ammonium methosulfate and the quantities of the perfume oil or the silicone derivative given in Table 3; total amount of softener rinse: 36 g; washing machine type Miele Novotronic W135; standard rinse program at a rinse temperature: 20° C. without a previous washing cycle.

TABLE 3

| Perfume oil | Product | washing wet | washing dry 1 day | washing dry 3 days | washing dry 7 days | washing dry 14 days |
|---|---|---|---|---|---|---|
| 0.9 parts by wt. Phenylethyl alcohol | 8 | 7 | 0 | 0 | 0 | 0 |
| 2.0 parts by wt. Silicone derivative A | 0 | 0 | 8 | 8 | 8 | 8 |

Preference for the intensity of the odor

For the wet washing, 1 evaluator could not distinguish any difference in the intensity of the odor.

Example 4

Basic material: 99 wt. % of a commercial perfume-free softener rinse comprising ca. 17 parts by weight Rewoquat® WE 18; (ditallow carboxyethyl)-hydroxyethyl methyl ammonium methosulfate and the quantities of the perfume oil or the silicone derivative given in Table 4; total amount of softener rinse: 36 g; washing machine type Miele Novotronic W135; standard rinse program at a rinse temperature: 20° C. without a previous washing cycle.

TABLE 4

| Perfume oil | Product | washing wet | washing dry 1 day | washing dry 3 days | washing dry 7 days | washing dry 14 days |
|---|---|---|---|---|---|---|
| 0.9 parts by wt. Phenylethyl alcohol | 7 | 8 | 2 | 0 | 0 | 0 |
| 2.43 parts by wt. Silicone derivative B | 1 | 0 | 5 | 7 | 6 | 8 |

Preference for the intensity of the odor

At 1 day and also at 3 days for the dry washing, one evaluator could not distinguish any difference in the intensity of each odor, for the 7 day dry washing, 2 evaluators could not distinguish any difference.

As the previous tests demonstrate, the product as such and the wet washing smell more intensively when the product is replaced by the pure phenylethyl alcohol. This is to be expected, as the pure phenylethyl alcohol has no inherent delayed release effect. On the other hand, when the dry washing is considered, it has a more intensive smell, particularly after longer times, i.e. after 7 or 14 days when the corresponding silicone derivative and not the pure phenylethyl alcohol is incorporated into the agent. The delayed release effect is demonstrated here by the silicone derivative that effects a sustained release of fragrance and thus provides a long lasting fragrance experience.

This proves that the silicone derivatives are capable of absorbing very well on the treated textiles and develop a long lasting fragrance effect there, due to their delayed release.

The invention claimed is:

1. A detergent, cleaning, conditioning or cosmetic agent comprising at least one oligomer, polymer or copolymer that comprises a structural element in accordance with Formula (1),

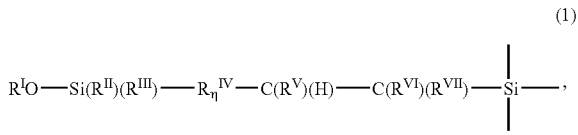

wherein $R^{II}$, $R^{III}$, independently of one another each stand for an aliphatic or aromatic, linear or branched, saturated or unsaturated, substituted or unsubstituted hydrocarbon group and wherein $R_\eta^{IV}$ stands for a hydrocarbon bridging member that is an aliphatic or aromatic, linear or branched, saturated or unsaturated, substituted or unsubstituted hydrocarbon group, wherein the number $\eta$ is 0 to 10, and wherein $R^V$, $R^{VI}$, $R^{VII}$, independently of each other each stand for hydrogen or an aliphatic or aromatic, linear or branched, saturated or unsaturated, substituted or unsubstituted hydrocarbon group, and wherein the terminal silicon in Formula 1 has its remaining three valences satisfied, independently of each other by any oligomeric, polymeric or copolymeric group, and wherein $R^IO$ represents either a group that is a fragrance alkoxy group and/or biocide alkoxy group that is derived from the corresponding fragrance alcohol and/or biocide alcohol $R^IOH$, represents a group that is derived from an enolizable fragrance- and/or biocide ester, ketone or aldehyde, and wherein the agent additionally comprises at least one compound that is absorbed on hard and/or soft substrate surfaces and carries at least one cationic charge.

2. The agent according to claim 1, wherein said agent is selected from the group consisting of a fragrant, biocidal and fragrant biocidal agent.

3. The agent according to claim 1, wherein the compound that is absorbed on hard and/or soft surfaces of substrates has a pH value in aqueous media of below 10.

4. The agent according to claim 1, comprising at least one silicone oligomer, polymer or copolymer, which on hydrolysis releases a fragrant and/or biocidal alcohol, aldehyde, ketone or ester.

5. The agent according to claim 4, wherein the fragrant and/or biocidal alcohol, aldehyde, ketone or ester is reacted with an olefinic halosilane or olefinic silicone alkoxide to form an olefinic silane.

6. The agent according to claim 4, wherein the olefinic silane is in accordance with Formula (2)

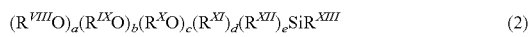

wherein $R^{VIII}O$, $R^{IX}O$ and $R^XO$, each independently of one another, represent fragrance alkoxy groups that derive from the corresponding fragrance alcohols $R^{VIII}OH$, $R^{IX}OH$ and $R^XOH$, wherein $R^{XI}$, $R^{XII}$ are selected from the group of $C_{1-40}$ monovalent unsaturated hydrocarbon groups and monovalent $C_{1-40}$ alkoxy groups, $R^{XIII}$ is a $C_{2-40}$ monovalent unsaturated hydrocarbon group with an olefinic end group, and a has a value from 1-3, b, c, d, e have values from 0-2, with the proviso that a+b+c+d+e=3 and a, b, c, d, e are whole numbers.

7. The agent according to claim 4, wherein the olefinic silane is in accordance with Formula (3)

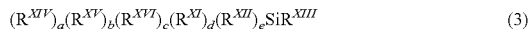

wherein $R^{XIV}$, $R^{XV}$ and $R^{XVI}$ each independently of one another have the Formula (4) $R^{XVII}(R^{XVIII})C=C(O-)R^{XIX}$ (4), $R^{XVII}$, $R^{XVIII}$ and $R^{XIX}$ independently of one another are chosen for each $R^{XIV}$, $R^{XV}$ and $R^{XVI}$; $R^{XI}$, $R^{XII}$ are selected from the group of $C_{1-40}$ monovalent unsaturated hydrocarbon groups and monovalent $C_{1-40}$ alkoxy groups, $R^{XIII}$ is a $C_{2-40}$ monovalent unsaturated hydrocarbon group with an olefinic end group, and a has a value from 1-3, b, c, d, e have values from 0-2, with the proviso that a+b+c+d+e=3 and a, b, c, d, e are whole numbers, and $R^{XVII}$, $R^{XVIII}$ and $R^{XIX}$ are selected from the group consisting of hydrogen and monovalent $C_{1-100}$ hydrocarbon groups.

8. The agent according to claim 7, wherein $R^{XIV}$, $R^{XV}$ and $R^{XVI}$ each independently of one another, possess the Formula (4) $R^{XVII}(R^{XVIII})C=(O-)-R^{XIX}$ (4) and derive from the group of the following aldehydes, ketones or esters, selected from 3-methyl-3(3-(1-methylethylphenyl))propanal), 2-methyl-3-(4-t-butylphenyl)propanal, 3-phenylpropional, 2-phenylpropional, propional, isobutyral, 2-methylbutyral, hexanal, octanal, nonanal, decanal, 3,7-dimethyl-1-al, p-tolylacetaldehyde, phenylacetaldehyde, 4-(3)(4-methyl-3-pentenyl)-3-cyclohexene-carbaldehyde, 2,6-dimethyl-5-heptenal, 3,7-dimethyl-2,6-octadienal, trans-4-decenal, cyclamen aldehyde, 4-(p-methoxyphenyl)-2-butanone, acetophenone, 2-pentanone, 2-butanone, 2-heptanone, 3-heptanone, 2-decanone, 3-penten-2-one, 6-methyl-5-hepten-2-one, geranyl acetone, 5-methyl-alpha-ionone, 2-acetonaphtone, 2-methyl-3-phenylpropan-2-yl acetate, linalyl acetate, menthanyl acetate, 2-phenylethyl acetate, tetrahydrolinalyl acetate, phenethyl propionate, phenethyl hexanoate, butyl acetate, phenoxyethyl isobutyrate, p-tert.-butylcyclohexyl acetate, linalyl acetate, dimethylbenzyl carbinyl acetate (DMBCA), phenylethyl acetate, benzyl acetate, ethylmethylphenyl glycinate, allylcyclohexyl propionate, styrallyl propionate, benzyl salicylate, cyclohexyl salicylate, floramate, melusate and jasmacyclate, linear alkanals having 8-18 carbon atoms, citral, citronellal, citronellyloxy-acetaldehyd, cyclamen aldehyd, lilial and bourgeonal, the ionones, α-isomethylionone and methyl cedryl ketone.

9. The agent according to claim 6, wherein the fragrance alkoxy groups and/or biocide alkoxy groups $R^{VIII}O$, $R^{IX}O$ and $R^XO$ are each derived from fragrance alcohols and/or biocide alcohols, selected from the group 2-methylbutanol, 3-pentanol, n-pentanol, 2-pentanol, n-hexanol, 2-methylpentanol, 1-decanol, sandela, nonadol, dimetol, thymol, 1-heptanol, menthol, eugenol, vanillin, o-vanillin, 4-(p-hydroxyphenyl)-2-butanone, syringe aldehyde, prenol, cis-3-hexanol, trans-3-hexanol, cis-4-heptenol, trans-2-octenol, trans-2-cis-6-nonadienol, nerol, ebanol, crotyl alcohol, oleyl alcohol, linalool, α-terpineol, β-phenethyl alcohol, cinnamyl alcohol, benzyl alcohol, α-methylbenzyl alcohol, nonyl alcohol, 1-octanol, 3-octanol, phenethyl salicylate, hydrocinnamyl alcohol, cis-6-nonen-1-ol, trans-2-nonen-1-ol, methyl salicylate, cis-3-octenol, anisyl alcohol, carvacrol, dihydrocarveol, benzyl salicylate, tetrahydrogeraniol, ethyl salicylate, ethyl vanillin, isoeugenol, isopulegol, lauryl alcohol, tetrahydrolinalool, 2-phenoxyethanol, citronellol, farnesol, and geraniol.

10. The agent according to claim 1, wherein the molecular weight of the oligomer, polymer or copolymer is up to about 300,000.

11. The agent, according to claim 1, wherein the content of the fragrance group or biocide group in the total weight of the oligomer, polymer or copolymer is up to 80 wt. %, based on the total agent.

12. The agent, according to claim 1, wherein the oligomer, polymer or copolymer is at least 50% linear.

13. The agent according to claim 1, wherein the oligomer, polymer or copolymer conform to Formula (5).

$$M_f M^F_g D_h D^F_i T_j T^F_k Q_l \quad (5)$$

with M: $R^{XX}R^{XXI}R^{XXII}SiO_{1/2}$; $M^F$: $R^{XX}RX^{XXI}R^FSiO_{1/2}$; D: $R^{XXIII}R^{XXIV}SiO_{2/2}$; $D^F$: $R^{XXIII}R^FSiO_{2/2}$; T: $R^{XXV}SiO_{3/2}$; $T^F$: $R^FSiO_{3/2}$ Q: $S_{4/2}$, wherein $R^{XX}$, $R^{XXI}$, $R^{XXII}$, $R^{XXIII}$, $R^{XXIV}$, $R^{XXV}$ each independently of one another, are selected for each M, $M^F$, D, $D^F$, T and $T^F$, from the group of $C_{1-40}$ monovalent, straight chain or branched, saturated or unsaturated alkyl or alkoxy groups or from the group of $C_{1-40}$ monovalent aryl or aryloxy groups, wherein the alkyl, alkoxy, aryl, aryloxy groups can be substituted, wherein f, g are positive numbers, h, i, j, k, l are positive numbers or equal to zero, wherein at least one of h, i, j, k, l is not equal to zero and at least one of g, i, or k equals 1 or is greater than 1, and wherein $R^F$ is derived from one of the abovementioned groups $(R^{VIII}O)_a(R^{IV}O)_b(R^XO)_c(R^{XI}_{XIV})_d(R^{XII})_eSiR^{XIII}$ (according to Formula (2)) and/or $(R^{...})_a(R^{XV})_b(R^{XVI})_c (R^{XI})_d(R^{XII})_eSiR^{XIII}$ (according to Formula (3)), wherein this group $R^F$ is bonded through a bivalent $C_{2-40}$ hydrocarbon bridging member, derived from $R^{XIII}$ (a $C_{2-40}$ monovalent unsaturated hydrocarbon group with an olefinic end group) with a Si-atom of the oligomer, polymer or copolymer.

14. The agent according to claim 1, wherein the oligomer, polymer copolymer is selected from the following Formulae:

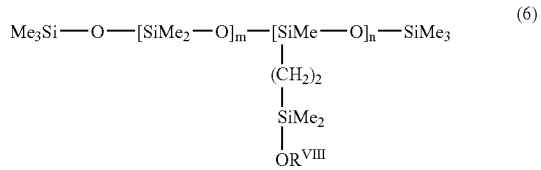

(6)

wherein $OR^{VIII}$ stands for a fragrance alkoxy group or biocide alkoxy group, particularly for a phenylethyl alcohol group, and wherein m and n each have a positive value, with the limitation that the resulting silicone reaches a molecular weight of at least 150.
and/or $$R^{VIII}O-SiMe_2-(CH_2)_2-[SiMe_2-O]_p-SiMe_2- (CH_2)_2-SiMe_2-OR^{VIII} \quad (7)$$

wherein $OR^{VIII}$ stands for a fragrance alkoxy group or biocide alkoxy group, particularly for a phenylethyl alcohol group, with p greater than 0, with the limitation that the resulting silicone reaches a molecular weight of at least 150.

15. The agent according to claim 1, wherein the oligomer, polymer or copolymer is comprised in the agent in amounts of greater than 0.001 wt. %, based on the total agent.

16. The agent according to claim 1, wherein the compound that preferably carries at least one cationic charge and is absorbed on hard and/or soft surfaces of substrates is preferably comprised in amounts of greater than 0.01 wt. %, based on the total agent.

17. The agent according to claim 1, wherein the compound that carries at least one cationic charge and is absorbed on hard and/or soft surfaces of substrates is a compound that is selected from the group consisting of cationic and amphoteric emulsifiers, cationic surfactants, zwitterionic compounds, ampholytes, amphosurfactants, betaines and cationic and amphoteric polymers.

18. The agent according to claim 1, wherein the compound that is absorbed on hard and/or soft surfaces of substrates, is a compound that in aqueous media at pH-values below 4 possesses at least one cationic charge.

19. The agent according to claim 1, wherein the compound that is absorbed on hard and/or soft surfaces of substrates is a quaternary ammonium compound, in which at least one alkyl chain is interrupted by an ester group and/or amido group.

20. The agent according to claim 1, wherein the compound that is absorbed on hard and/or soft surfaces of substrates is a quaternary ammonium compound selected from the following Formula (9):

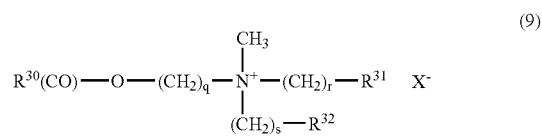

(9)

wherein, $R^{30}$ stands for an aliphatic alkyl group with 12 to 22 carbon atoms and 0, 1, 2 or 3 double bonds, $R^{31}$ stands for H, OH or $O(CO)R^a$, $R^{32}$ independently of $R^{31}$ stands for H, OH or $O(CO)R^b$, wherein $R^a$ and $R^b$, independently of each other, each stand for an aliphatic alkyl group having 12 to 22 carbon atoms with 0, 1, 2 or 3 double bonds, q, r and s independently of each other can each have the value 1, 2 or 3, X is an adequate anion, and/or from the Formula (12):

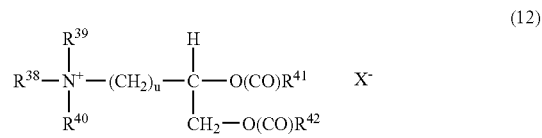

(12)

wherein $R^{38}$, $R^{39}$ and $R^{40}$ independently of one another stand for a $C_{1-4}$ alkyl, alkenyl or hydroxyalkyl group, $R^{41}$ and $R^{42}$, each independently selected, represents a $C_{8-28}$ alkyl group with 0, 1, 2 or 3 double bonds and u is a number between 0 and 5, $X^-$ is an adequate anion, preferably a halide, methosulfate, methophosphate or phosphate ion as well as mixtures thereof.

21. The agent according to claim 1, wherein the compound that is absorbed on hard and/or soft surfaces of substrates is selected from the group consisting of N-methyl-N(2-hydroxyethyl)-N,N-(ditallow acyloxyethyl) ammonium methosulfate and N-methyl-N(2-hydroxyethyl)-N,N-(dipalmitoylethyl) ammonium methosulfate.

22. The agent according to claim 1, wherein the compound that is absorbed on hard and/or soft surfaces of substrates and which preferably carries at least one cationic charge is a zwitterionic compound according to Formula (18)

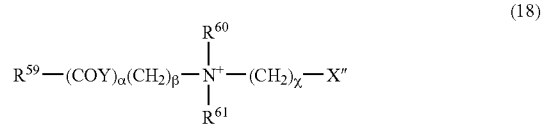

(18)

in which $R^{59}$ stands for a $C_{6-28}$ alkyl or alkenyl group, $R^{60}$ and $R^{61}$ are each, independently of one another, $C_{1-4}$ alkyl groups; α stands for the number 0 or 1, β and χ are each selected independently of one another from whole numbers from 1 to 4 and Y is oxygen or nitrogen and X is an anion.

23. The agent according to claim 1, wherein the compound that is absorbed on hard and/or soft surfaces of substrates and which preferably carries at least one cationic charge is an alkylamido alkylene dimethylcarboxylic acid-betaine according to Formula (19):

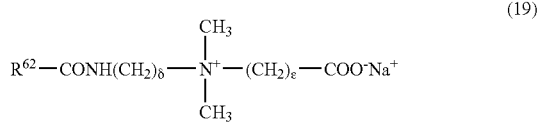

(19)

wherein δ and ε, independently of one another, are whole numbers from 1-4, advantageously δ is equal to 2 or 3 and ε equals 2 or 3 and $R^{62}$ stands for a $C_{10-18}$ alkyl chain or mixtures thereof.

24. The agent according to claim 1, wherein the compound that is absorbed on hard and/or soft surfaces of substrates and which preferably carries at least one cationic charge is a cationic nitrile according to Formula (14):

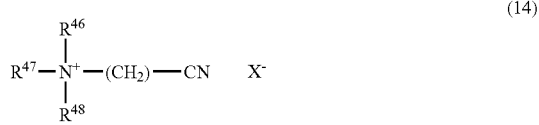

(14)

in which $R^{46}$ stands for —H, —$CH_3$, a $C_{2-24}$ alkyl or alkenyl group, a substituted $C_{2-24}$ alkyl or alkenyl group having at least one substituent from the group of —Cl, —Br, —OH, —$NH_2$, —CN, an alkyl or alkenylaryl group having a $C_{1-24}$ alkyl group or for a substituted alkyl or alkenylaryl group having a $C_{1-24}$ alkyl group and at least a further substituent on the aromatic ring, $R^{47}$ and $R^{48}$, independently of one another are selected from —$CH_2$—CN, —$CH_3$, —$CH_2$—$CH_3$, —$CH_2$—$CH_2$—$CH_3$, —$CH(CH_3)$—$CH_3$, —$CH_2$—OH, —$CH_2$—$CH_2$—OH, —$CH(OH)$—$CH_3$, —$CH_2$—$CH_2$—$CH_2$—OH, —$CH_2$—$CH(OH)$—$CH_3$, —$CH(OH)$—$CH_2$—$CH_3$, —$(CH_2CH_2$—$O)_n$H with n equal to 1, 2, 3, 4, 5 or 6 and X is an anion.

25. The agent according to claim 1, comprising at least one cationic nitrile according to Formula (15).

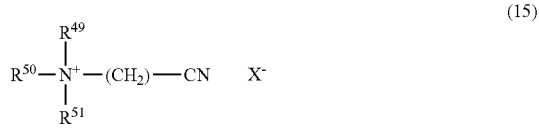

(15)

in which $R^{49}$, $R^{50}$ and $R^{51}$ independently of one another are selected from —$CH_3$, —$CH_2$—$CH_3$, —$CH_2$—$CH_2$—$CH_3$, —$CH(CH_3)$—$CH_3$, wherein $R^{49}$ can also be —H and X is an anion.

26. The agent according to claim 25, wherein $X^-$ stands for an anion that is selected from the group consisting of chloride, bromide, iodide, hydrogen sulfate, methosulfate, lauryl sulfate, dodecylbenzene sulfonate, p-toluene sulfonate (tosylate), cumene sulfonate or xylene sulfonate or mixtures thereof 27. The agent according to claim 1, wherein the agent is present in solid, dispersed, powder, granular or compressed form.

28. The agent according to claim 1, wherein the agent comprises up to 95 wt. % of at least one solvent.

29. The agent according to claim 1, wherein the agent comprises at least one further substance selected from the group consisting of surfactants, inorganic and organic builders, bleaching agents, bleach activators, bleach stabilizers, bleach catalysts, enzymes, special polymers, polymers with cobuilder properties, graying inhibitors, optical brighteners, UV-protection agents, soil repellents, electrolytes, colorants, perfumes, fragrances, perfume carriers, pH adjustors, chelating agents, fluorescence agents, foam inhibitors, anti-creasing agents, antioxidants, quaternary ammonium compounds, antistatics, ironing auxiliaries, UV-absorbers, antiredeposition agents, germicides, antimicrobials, fungicides, viscosity regulators, pearlizers, color-transfer inhibitors, anti-shrinkage agents, corrosion inhibitors, conservation agents, softeners, softening rinse agents, protein hydrolyzates, water-proofing and impregnation agents, hydrotropes, silicone oils, swelling agents and non-slip agents.

30. The agent according to claim 1, wherein the agent is a cosmetic agent.

31. The agent according to claim 1, wherein the agent is a textile treatment agent.

32. The agent according to claim 1 wherein the agent is a conditioning agent for keratinous fibers.

33. A process for treating hard and/or soft substrate surfaces comprising the step of applying an effective quantity of the agent according to claim 1 to the substrate to be treated by means of a spray dispenser, wherein.the agent is present in liquid form.

34. The agent according to claim 1 where the agent is a cleaning agent for hard surfaces.

35. A product, comprising the agent according to claim 1 and a spray dispenser.

36. A conditioning substrate, wherein the substrate is saturated and/or coated with a detergent, cleaning, conditioning or cosmetic agent comprising at least one oligomer, polymer or copolymer that comprises a structural element in accordance with Formula (1),

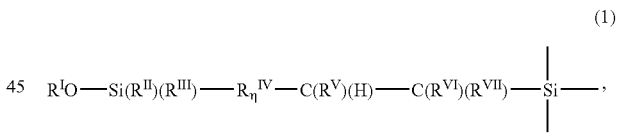

(1)

wherein $R^{II}$, $R^{III}$, independently of one another each stand for an aliphatic or aromatic, linear or branched, saturated or unsaturated, substituted or unsubstituted hydrocarbon group that, as appropriate, can comprise heteroatoms such as oxygen, nitrogen, sulfur or halogens or others and wherein $R_\eta^{IV}$ stands for a hydrocarbon bridging member that is an aliphatic or aromatic, linear or branched, saturated or unsaturated, substituted or unsubstituted hydrocarbon group, wherein the number η is 0 to 10, and wherein $R^V$, $R^{VI}$, $R^{VII}$, independently of each other each stand for hydrogen or an aliphatic or aromatic, linear or branched, saturated or unsaturated, substituted or unsubstituted hydrocarbon group and wherein the terminal silicon in Formula 1 has its remaining three valences satisfied, independently of each other by any oligomeric, polymeric or copolymeric group, and wherein $R^IO$ represents either a group that is a fragrance alkoxy group and/or biocide alkoxy group that is derived from the corresponding fragrance alcohol and/or biocide alcohol $R^IOH$, or wherein $R^IO$ represents a group that is derived from an enolizable fragrance- and/or biocide ester, ketone or aldehyde, and wherein the agent additionally comprises at least one compound that is absorbed on hard and/or soft substrate surfaces surfaces and carries at least one cationic charge.

37. The conditioning substrate according to claim 36, wherein the substrate consists of a fleece material.

38. The conditioning substrate according to claim 36, wherein the substrate has a grammage between 20 to 1000 g/m².

39. The conditioning substrate according to claim 36, wherein the substrate has a size of 0.2 to 0.005 m².

40. A process for conditioning textiles, wherein at least one conditioning substrate according to claim 36 is treated in a textile-drying process.

41. A compound that carries at least one cationic charge and which is absorbed on hard and/or soft surfaces of substrates, to fix an oligomer, polymer or copolymer that comprises the following structural element shown in Formula (1) on hard and/or soft substrate surfaces:

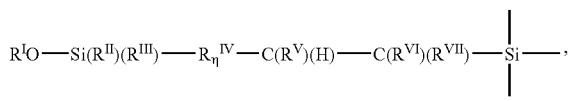

(1)

wherein $R^{II}$, $R^{III}$, independently of one another each stand for an aliphatic or aromatic, linear or branched, saturated or unsaturated, substituted or unsubstituted hydrocarbon group and wherein $R_\eta^{IV}$ stands for a hydrocarbon bridging member that is an aliphatic or aromatic, linear or branched, saturated or unsaturated, substituted or unsubstituted hydrocarbon group wherein the number $\eta$ is 0 to 10, and wherein $R^V$, $R^{VI}$, $RV^{II}$, independently of each other each stand for hydrogen or an aliphatic or aromatic, linear or branched, saturated or unsaturated, substituted or unsubstituted hydrocarbon group, and wherein the terminal silicon in Formula 1 has its remaining three valences satisfied, independently of each other by any oligomeric, polymeric or copolymeric group, and wherein $R^I O$ represents either a group that is a fragrance alkoxy group and/or biocide alkoxy group that is derived from the corresponding fragrance alcohol and/or biocide alcohol $R^I OH$, or wherein $R^I O$ represents a group that is derived from an enolizable fragrance- and/or biocide ester, ketone or aldehyde and wherein the agent additionally comprises at least one compound that is absorbed on hard and/or soft substrate surfaces and carries at least one cationic charge.

42. The agent according to claim 1, wherein the compound that is absorbed on hard and/or soft surfaces is (ditallow carboxyethyl)-hydroxyethyl methyl ammonium methosulfate.

* * * * *